(12) United States Patent
Wang et al.

(10) Patent No.: US 10,125,184 B2
(45) Date of Patent: Nov. 13, 2018

(54) APOLIPOPROTEIN E POLYPEPTIDES AND THEIR USE

(71) Applicants: University of Pittsburgh—Of the Commonwealth System of Higher Education, Pittsburgh, PA (US); University of South Carolina, Columbia, SC (US)

(72) Inventors: Tony Tianyi Wang, Harrisonburg, VA (US); Shufeng Liu, Pittsburgh, PA (US); Fan Daping, Columbia, SC (US)

(73) Assignees: UNIVERSITY OF PITTSBURGH—OF THE COMMONWEALTH SYSTEM OF HIGHER EDUCATION, Pittsburgh, PA (US); UNIVERSITY OF SOUTH CAROLINA, Columbia, SC (US)

( * ) Notice: Subject to any disclaimer, the term of this patent is extended or adjusted under 35 U.S.C. 154(b) by 0 days.

(21) Appl. No.: 14/952,781

(22) Filed: Nov. 25, 2015

(65) Prior Publication Data

US 2016/0108104 A1 Apr. 21, 2016

Related U.S. Application Data

(62) Division of application No. 14/232,603, filed as application No. PCT/US2012/047684 on Jul. 20, 2012, now Pat. No. 9,234,026.

(60) Provisional application No. 61/510,387, filed on Jul. 21, 2011.

(51) Int. Cl.
| | | |
|---|---|---|
| *A61K 38/17* | (2006.01) | |
| *A61K 38/00* | (2006.01) | |
| *A61K 45/06* | (2006.01) | |
| *C07K 14/775* | (2006.01) | |

(52) U.S. Cl.
CPC ........ *C07K 14/775* (2013.01); *A61K 38/1709* (2013.01); *A61K 45/06* (2013.01); *A61K 38/00* (2013.01)

(58) Field of Classification Search
CPC .... A61K 38/00; A61K 38/1709; A61K 45/06; C07K 14/775
See application file for complete search history.

(56) References Cited

U.S. PATENT DOCUMENTS

| | | |
|---|---|---|
| 7,691,382 B2 | 4/2010 | Dobson |
| 2007/0117746 A1 | 3/2007 | Dobson |
| 2009/0048171 A1 | 2/2009 | Dobson |
| 2009/0169598 A1 | 7/2009 | Crutcher |
| 2010/0221273 A1 | 9/2010 | Dobson |
| 2010/0310533 A1 | 12/2010 | Luo |

FOREIGN PATENT DOCUMENTS

| | | | | |
|---|---|---|---|---|
| WO | WO 9210512 A1 * | 6/1992 | ........... | C07K 14/775 |
| WO | WO 2002/048388 A2 | 6/2002 | | |
| WO | WO 2005/082399 A2 | 9/2005 | | |
| WO | WO 2011085110 A1 * | 7/2011 | ........... | C07K 14/775 |

OTHER PUBLICATIONS

Uniprot Protein Database, protein accession P02649, accessed on Nov. 17, 2016.*
Azuma et al., "A synthetic peptide of human apoprotein E with antibacterial activity," *Peptides* 21:327-330 (2000).
Clay et al., "Localization of a domain in apolipoprotein E with both cytostatic and cytotoxic activity," *Biochemistry* 34:11142-11151 (1995).
Dobson et al., "The receptor-binding region of human apolipoprotein E has direct anti-infective activity," *The Journal of Infectious Diseases* 193:442-450 (Feb. 1, 2006).
Dyer et al., "Structural features of synthetic peptides of apolipoprotein E that bind the LDL receptor," *Journal of Lipid Research* 36(1):80-88 (Jan. 1995).
International Search Report from parent PCT Application No. PCT/US2012/047684, 7 pages (dated Nov. 8, 2012).
Kelly et al., "Anti-infective activity of apolipoprotein domain derived peptides in vitro: identification of novel antimicrobial peptides related to apolipoprotein B with anti-HIV activity," *BMC Immunology* 11:13 (2010).
Kelly et al., "Apolipoprotein E-derived antimicrobial peptide analogues with altered membrane affinity and increased potency and breadth of activity," *FEBS Journal* 274:4511-4525 (2007).
Liu et al., "Human apolipoprotein E peptides inhibit hepatitis C virus entry by blocking virus binding," *Hepatology* 56(2):484-491 (Jul. 2012).
Liu et al., "Human apolipoprotein E peptides inhibit hepatitis C virus entry by blocking virus binding," *Hepatology* 56(2):484-491 (Nov. 2, 2012).
Mayo Clinic website, Hepatitis C treatment, www.mayoclinic.org/diseases-conditions/hepatitis-c/basics/treament/con-200306018, accessed on Feb. 4, 2015.
Mims et al., "A nonexchangeable apolipoprotein E peptide that mediates binding to the low density lipoprotein receptor," *Journal of Biological Chemistry* 269(32):20539-20547 (Aug. 1994).

(Continued)

*Primary Examiner* — Rachael E Bredefeld
*Assistant Examiner* — Erinne R Dabkowski
(74) *Attorney, Agent, or Firm* — Klarquist Sparkman, LLP

(57) ABSTRACT

Disclosed herein are several apoplipoprotein E (ApoE) polypeptides, and nucleic acids encoding these polypeptides, that can be used to treat or prevent a hepatitis infection in a subject, such as a hepatitis C virus infection. These ApoE polypeptides can inhibit the entry of hepatitis C virus into cells, and inhibit viral replication. Nucleic acids encoding these polypeptides are also disclosed, as well as methods.

15 Claims, 12 Drawing Sheets

Figure 2E:
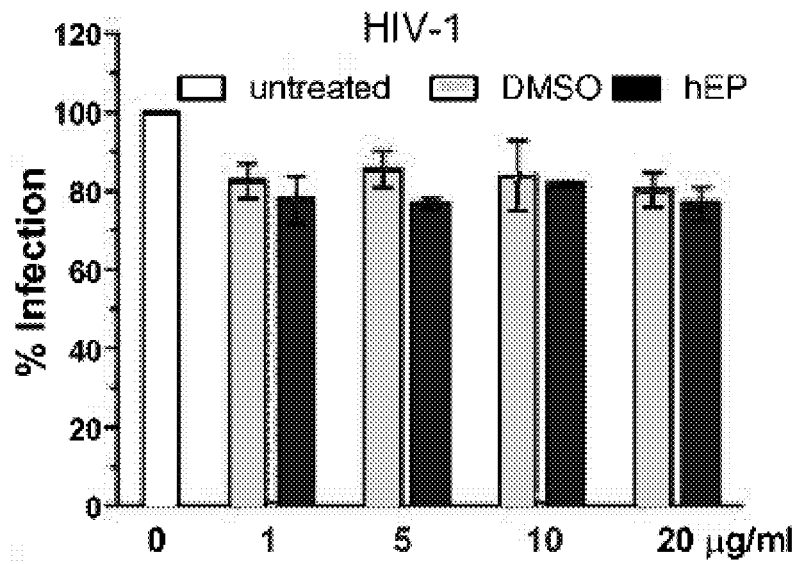
Figure 2F:
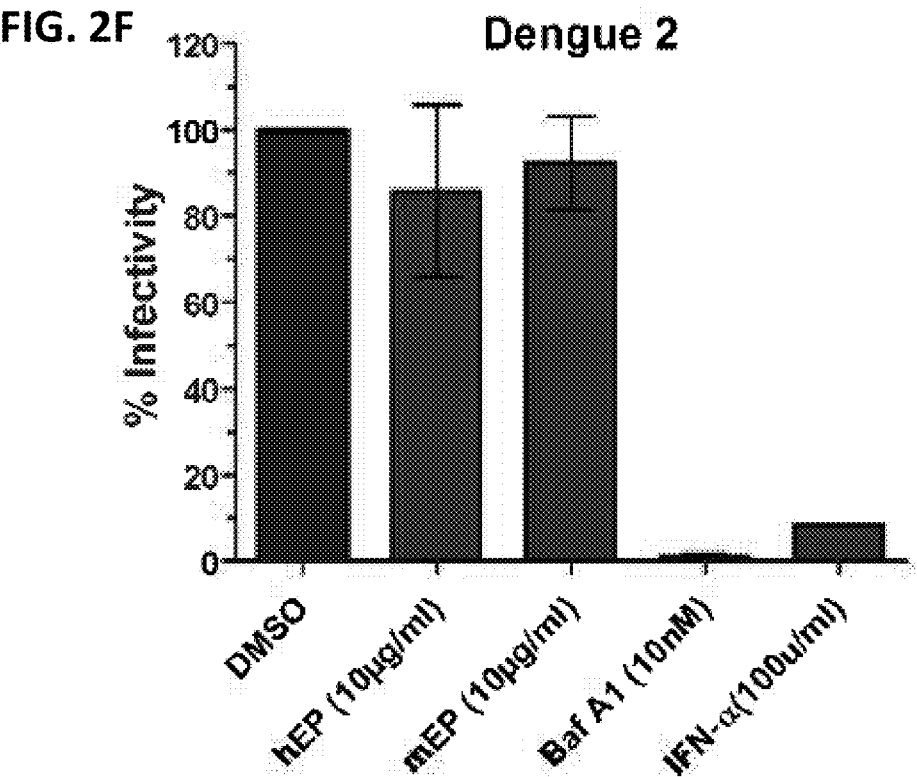

Specification includes a Sequence Listing.

(56) References Cited

OTHER PUBLICATIONS

Owen et al., "Apolipoprotein E on hepatitis C virion facilitates infection through interaction with low-density lipoprotein receptor," *Virology* 394(1):99-108 (Nov. 10, 2009).
Raussens et al., "Structural characterization of a low density lipoprotein receptor-active apolipoprotein E peptide, ApoE3-(126-183)," *Journal of Biological Chemistry* 275(49):38329-36 (Dec. 2000).
Written Opinion from parent PCT Application No. PCT/US2012/047684, 7 pages (dated Nov. 8, 2012).

* cited by examiner

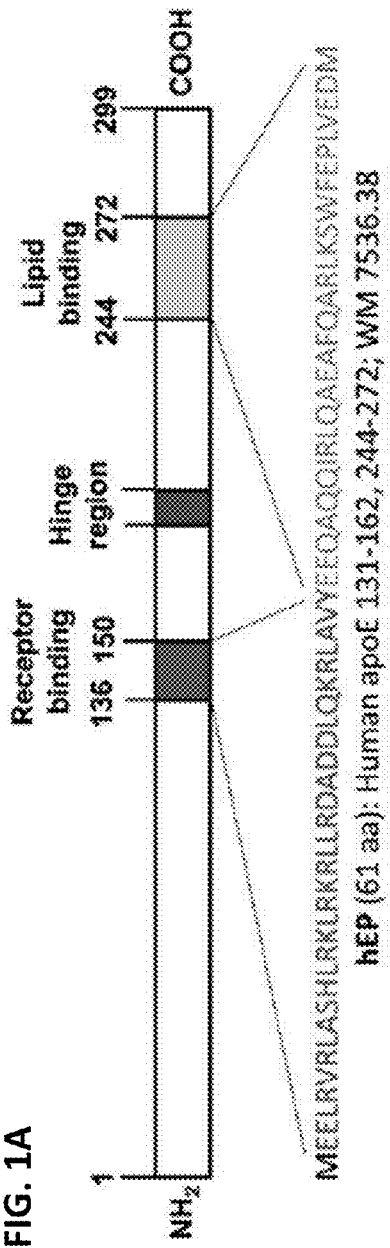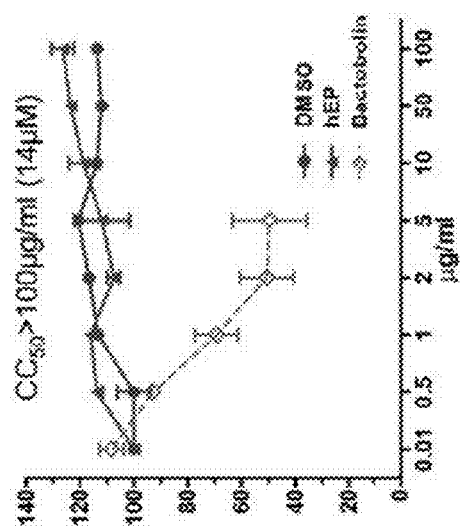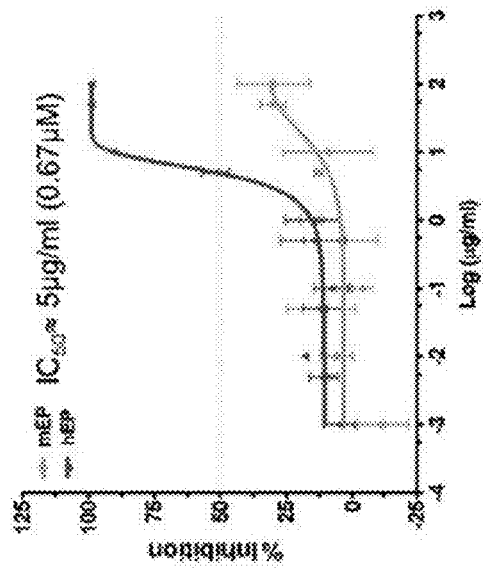
FIG. 1A
FIG. 1B
FIG. 1C

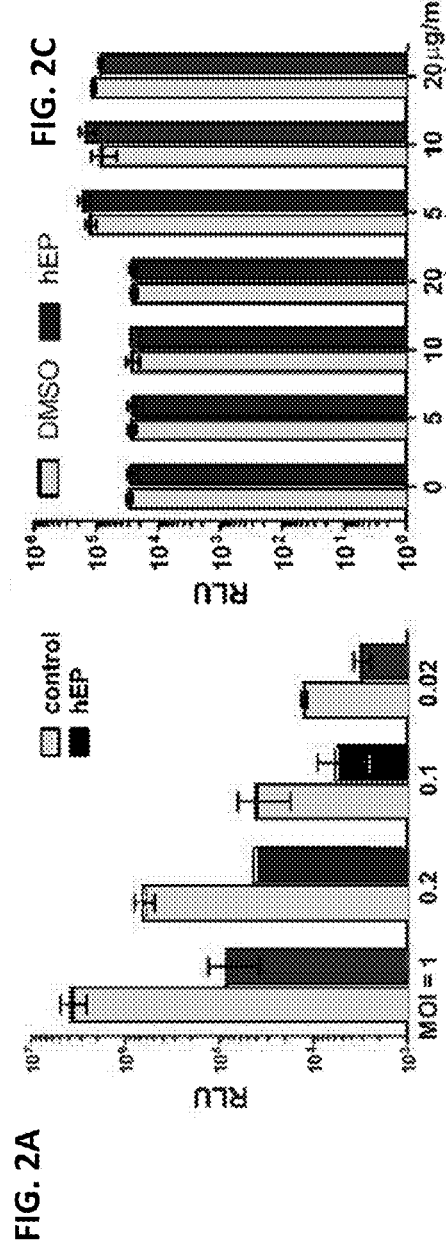
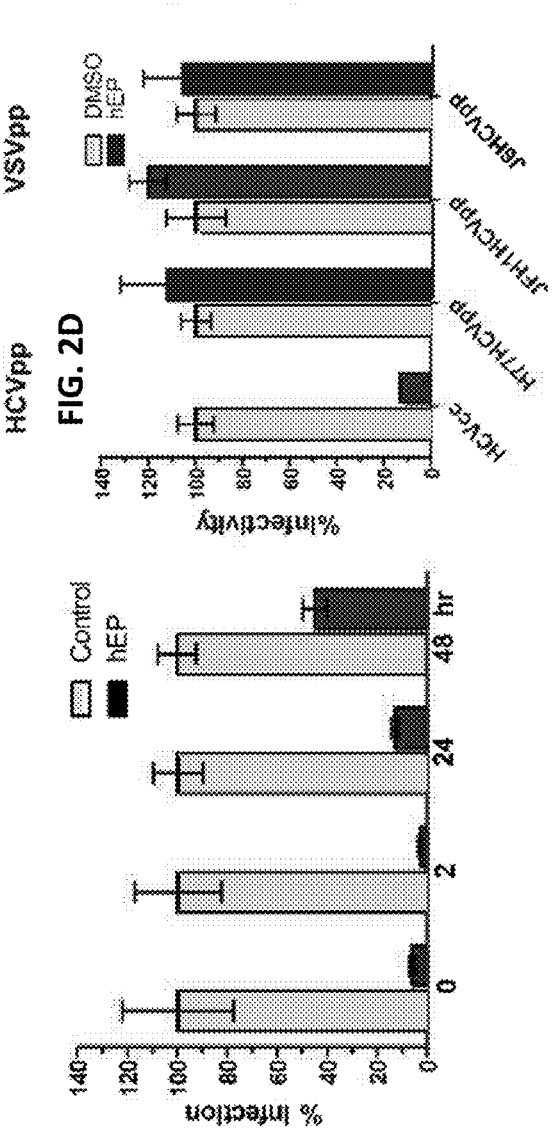
FIG. 2A
FIG. 2B
FIG. 2C
FIG. 2D

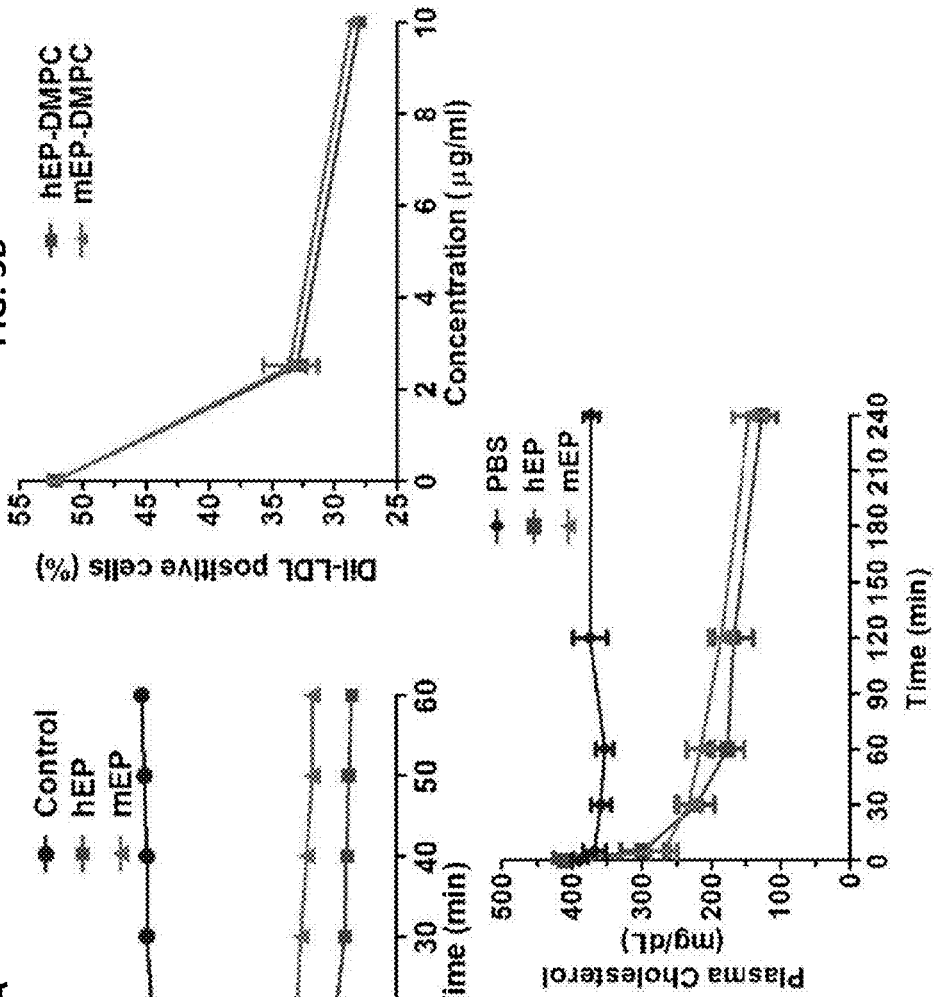

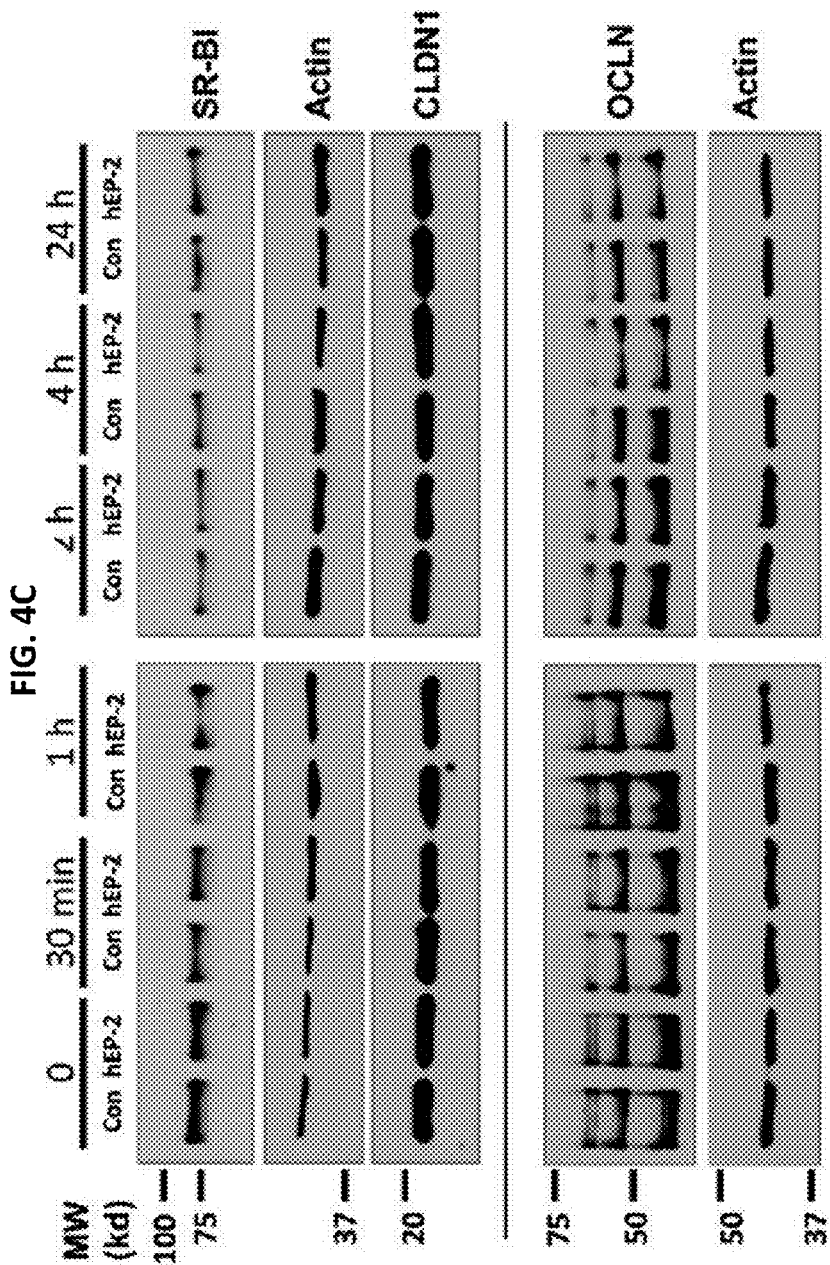

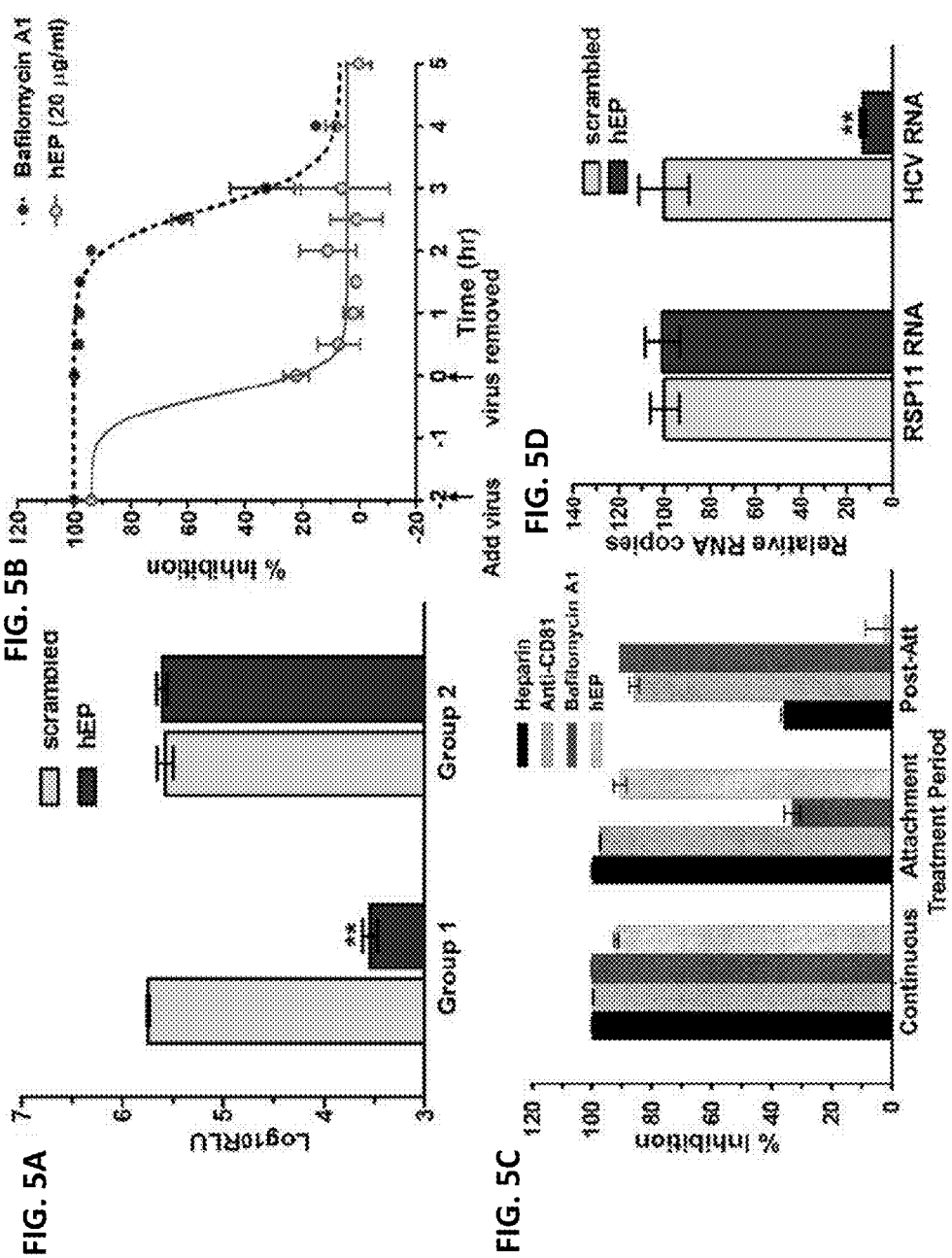

FIG. 6

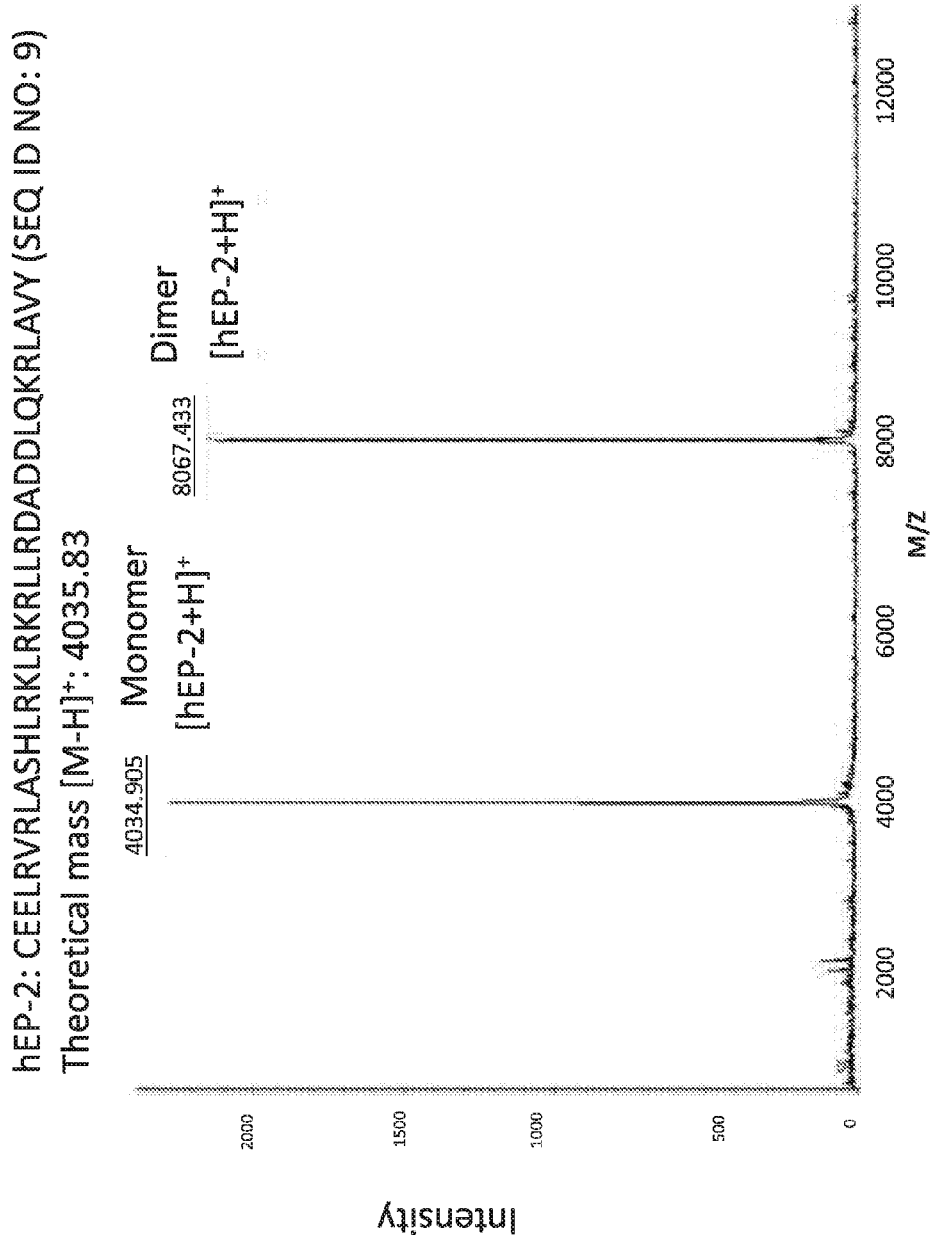

SEQUENCE LISTING

<160> NUMBER OF SEQ ID NOS: 24

<210> SEQ ID NO 1
<211> LENGTH: 28
<212> TYPE: PRT
<213> ORGANISM: Homo sapiens

<400> SEQUENCE: 1

Val Arg Leu Ala Ser His Leu Arg Lys Leu Arg Lys Arg Leu Leu Arg
1               5                   10                  15

Asp Ala Asp Leu Gln Lys Arg Leu Ala Val Tyr
            20                  25

<210> SEQ ID NO 2
<211> LENGTH: 32
<212> TYPE: PRT
<213> ORGANISM: Homo sapiens

<400> SEQUENCE: 2

Glu Glu Leu Arg Val Arg Leu Ala Ser His Leu Arg Lys Leu Arg Lys
1               5                   10                  15

Arg Leu Leu Arg Asp Ala Asp Leu Gln Lys Arg Leu Ala Val Tyr
            20                  25                  30

<210> SEQ ID NO 3
<211> LENGTH: 317
<212> TYPE: PRT
<213> ORGANISM: Homo sapiens

<400> SEQUENCE: 3

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
            35                  40                  45

Gly Arg Phe Trp Asp Tyr Leu Arg Trp Val Gln Thr Leu Ser Glu Gln
        50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125

Val Arg Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
        195                 200                 205

Arg Ala Ala Thr Val Gly Ser Leu Ala Gly Gln Pro Leu Gln Glu Arg
210                 215                 220

```
Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
            245                 250                 255

Val Arg Ala Lys Leu Glu Glu Gln Ala Gln Gln Ile Arg Leu Gln Ala
        260                 265                 270

Glu Ala Phe Gln Ala Arg Leu Lys Ser Trp Phe Glu Pro Leu Val Glu
    275                 280                 285

Asp Met Gln Arg Gln Trp Ala Gly Leu Val Glu Lys Val Gln Ala Ala
290                 295                 300

Val Gly Thr Ser Ala Ala Pro Val Pro Ser Asp Asn His
305                 310                 315

<210> SEQ ID NO 4
<211> LENGTH: 311
<212> TYPE: PRT
<213> ORGANISM: Mus musculus

<400> SEQUENCE: 4

Met Lys Ala Leu Trp Ala Val Leu Leu Val Thr Leu Leu Thr Gly Cys
1               5                   10                  15

Leu Ala Glu Gly Glu Pro Glu Val Thr Asp Gln Leu Glu Trp Gln Ser
            20                  25                  30

Asn Gln Pro Trp Glu Gln Ala Leu Asn Arg Phe Trp Asp Tyr Leu Arg
        35                  40                  45

Trp Val Gln Thr Leu Ser Asp Gln Val Gln Glu Glu Leu Gln Ser Ser
50                  55                  60

Gln Val Thr Gln Glu Leu Thr Ala Leu Met Glu Asp Thr Met Thr Glu
65                  70                  75                  80

Val Lys Ala Tyr Lys Lys Glu Leu Glu Glu Gln Leu Gly Pro Val Ala
                85                  90                  95

Glu Glu Thr Arg Ala Arg Leu Gly Lys Glu Val Gln Ala Ala Gln Ala
            100                 105                 110

Arg Leu Gly Ala Asp Met Glu Asp Leu Arg Asn Arg Leu Gly Gln Tyr
        115                 120                 125

Arg Asn Glu Val His Thr Met Leu Gly Gln Ser Thr Glu Glu Ile Arg
130                 135                 140

Ala Arg Leu Ser Thr His Leu Arg Lys Met Arg Lys Arg Leu Met Arg
145                 150                 155                 160

Asp Ala Asp Asp Leu Gln Lys Arg Leu Ala Val Tyr Lys Ala Gly Ala
                165                 170                 175

Arg Glu Gly Ala Glu Arg Gly Val Ser Ala Ile Arg Glu Arg Leu Gly
            180                 185                 190

Pro Leu Val Glu Gln Gly Arg Gln Arg Thr Ala Asn Leu Gly Ala Gly
        195                 200                 205

Ala Ala Gln Pro Leu Arg Asp Arg Ala Gln Ala Phe Gly Asp Arg Ile
    210                 215                 220

Arg Gly Arg Leu Glu Glu Val Gly Asn Gln Ala Arg Asp Arg Leu Glu
225                 230                 235                 240

Glu Val Arg Glu His Met Glu Glu Val Arg Ser Lys Met Glu Glu Gln
                245                 250                 255

Thr Gln Gln Ile Arg Leu Gln Ala Glu Ile Phe Gln Ala Arg Leu Lys
            260                 265                 270

Gly Trp Phe Glu Pro Ile Val Glu Asp Met His Arg Gln Trp Ala Asn
```

```
                275                 280                 285
Leu Met Glu Lys Ile Gln Ala Ser Val Ala Thr Asn Pro Ile Ile Thr
    290                 295                 300

Pro Val Ala Gln Glu Asn Gln
305                 310

<210> SEQ ID NO 5
<211> LENGTH: 29
<212> TYPE: PRT
<213> ORGANISM: Homo sapiens

<400> SEQUENCE: 5

Glu Glu Gln Ala Gln Gln Ile Arg Leu Gln Ala Glu Ala Phe Gln Ala
1               5                   10                  15

Arg Leu Lys Ser Trp Phe Glu Pro Leu Val Glu Asp Met
            20                  25

<210> SEQ ID NO 6
<211> LENGTH: 61
<212> TYPE: PRT
<213> ORGANISM: Homo sapiens

<400> SEQUENCE: 6

Glu Glu Leu Arg Val Arg Leu Ala Ser His Leu Arg Lys Leu Arg Lys
1               5                   10                  15

Arg Leu Leu Arg Asp Ala Asp Asp Leu Gln Lys Arg Leu Ala Val Tyr
            20                  25                  30

Glu Glu Gln Ala Gln Gln Ile Arg Leu Gln Ala Glu Ala Phe Gln Ala
        35                  40                  45

Arg Leu Lys Ser Trp Phe Glu Pro Leu Val Glu Asp Met
    50                  55                  60

<210> SEQ ID NO 7
<211> LENGTH: 56
<212> TYPE: PRT
<213> ORGANISM: Homo sapiens

<400> SEQUENCE: 7

Arg Leu Ala Ser His Leu Arg Lys Leu Arg Lys Arg Leu Leu Arg Asp
1               5                   10                  15

Ala Asp Asp Leu Gln Lys Arg Leu Ala Val Tyr Glu Glu Gln Ala Gln
            20                  25                  30

Gln Ile Arg Leu Gln Ala Glu Ala Phe Gln Ala Arg Leu Lys Ser Trp
        35                  40                  45

Phe Glu Pro Leu Val Glu Asp Met
    50                  55

<210> SEQ ID NO 8
<211> LENGTH: 29
<212> TYPE: PRT
<213> ORGANISM: Homo sapiens

<400> SEQUENCE: 8

Cys Val Arg Leu Ala Ser His Leu Arg Lys Leu Arg Lys Arg Leu Leu
1               5                   10                  15

Arg Asp Ala Asp Asp Leu Gln Lys Arg Leu Ala Val Tyr
            20                  25

<210> SEQ ID NO 9
<211> LENGTH: 33
```

```
<212> TYPE: PRT
<213> ORGANISM: Homo sapiens

<400> SEQUENCE: 9

Cys Glu Glu Leu Arg Val Arg Leu Ala Ser His Leu Arg Lys Leu Arg
1               5                   10                  15

Lys Arg Leu Leu Arg Asp Ala Asp Asp Leu Gln Lys Arg Leu Ala Val
            20                  25                  30

Tyr

<210> SEQ ID NO 10
<211> LENGTH: 22
<212> TYPE: PRT
<213> ORGANISM: Homo sapiens

<400> SEQUENCE: 10

Cys Val Arg Leu Ala Ser His Leu Arg Lys Leu Arg Lys Arg Leu Leu
1               5                   10                  15

Arg Asp Ala Asp Asp Leu
            20

<210> SEQ ID NO 11
<211> LENGTH: 21
<212> TYPE: PRT
<213> ORGANISM: Homo sapiens

<400> SEQUENCE: 11

Cys Ile Arg Leu Gln Ala Glu Ala Phe Gln Ala Arg Leu Lys Ser Trp
1               5                   10                  15

Phe Glu Pro Leu Val
            20

<210> SEQ ID NO 12
<211> LENGTH: 41
<212> TYPE: PRT
<213> ORGANISM: Homo sapiens

<400> SEQUENCE: 12

Val Arg Leu Ala Ser His Leu Arg Lys Leu Arg Lys Arg Leu Leu Arg
1               5                   10                  15

Asp Ala Asp Asp Leu Ile Arg Leu Gln Ala Glu Ala Phe Gln Ala Arg
            20                  25                  30

Leu Lys Ser Trp Phe Glu Pro Leu Val
        35                  40

<210> SEQ ID NO 13
<211> LENGTH: 30
<212> TYPE: PRT
<213> ORGANISM: Homo sapiens

<400> SEQUENCE: 13

Leu Arg Val Arg Leu Ala Ser His Leu Arg Lys Leu Arg Lys Arg Leu
1               5                   10                  15

Leu Arg Asp Ala Asp Asp Leu Gln Lys Arg Leu Ala Val Tyr
            20                  25                  30

<210> SEQ ID NO 14
<211> LENGTH: 25
<212> TYPE: PRT
<213> ORGANISM: Homo sapiens

<400> SEQUENCE: 14
```

Glu Glu Leu Arg Val Arg Leu Ala Ser His Leu Arg Lys Leu Arg Lys
1               5                   10                  15

Arg Leu Leu Arg Asp Ala Asp Asp Leu
            20                  25

<210> SEQ ID NO 15
<211> LENGTH: 28
<212> TYPE: PRT
<213> ORGANISM: Homo sapiens

<400> SEQUENCE: 15

Val Arg Leu Ala Ser His Leu Arg Lys Leu Arg Lys Arg Leu Leu Arg
1               5                   10                  15

Asp Ala Asp Asp Leu Gln Lys Arg Leu Ala Val Tyr
            20                  25

<210> SEQ ID NO 16
<211> LENGTH: 24
<212> TYPE: PRT
<213> ORGANISM: Homo sapiens

<400> SEQUENCE: 16

Cys Leu Arg Val Arg Leu Ala Ser His Leu Arg Lys Leu Arg Lys Arg
1               5                   10                  15

Leu Leu Arg Asp Ala Asp Asp Leu
            20

<210> SEQ ID NO 17
<211> LENGTH: 12
<212> TYPE: PRT
<213> ORGANISM: Homo sapiens

<400> SEQUENCE: 17

Cys Leu Arg Lys Leu Arg Lys Arg Leu Leu Arg Cys
1               5                   10

<210> SEQ ID NO 18
<211> LENGTH: 32
<212> TYPE: PRT
<213> ORGANISM: Homo sapiens

<400> SEQUENCE: 18

Glu Glu Leu Arg Val Arg Leu Ala Ser His Leu Arg Lys Leu Arg Lys
1               5                   10                  15

Arg Leu Leu Arg Asp Ala Asp Asp Leu Gln Lys Arg Leu Ala Val Tyr
            20                  25                  30

<210> SEQ ID NO 19
<211> LENGTH: 33
<212> TYPE: PRT
<213> ORGANISM: Homo sapiens

<400> SEQUENCE: 19

Cys Val Asp Arg Tyr Glu Ala Arg Leu Arg Ala Arg Ala Leu Lys Asp
1               5                   10                  15

Arg Gln Lys Arg Leu Leu Lys Glu Leu Ser Leu Leu Val Arg His Leu
            20                  25                  30

Asp

<210> SEQ ID NO 20
<211> LENGTH: 33

```
<212> TYPE: PRT
<213> ORGANISM: Mus musculus

<400> SEQUENCE: 20

Cys Glu Glu Ile Arg Ala Arg Leu Ser Thr His Leu Arg Lys Met Arg
1               5                   10                  15

Lys Arg Leu Met Arg Asp Ala Asp Asp Leu Gln Lys Arg Leu Ala Val
            20                  25                  30

Tyr

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gcctagccat ggcgttagta                                             20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
ctcccggggc actcgcaagc                                             20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
gccgagacta tctgcactac                                             20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
atgtccagcc tcagaacttc                                             20
```

APOLIPOPROTEIN E POLYPEPTIDES AND THEIR USE

CROSS REFERENCE TO RELATED APPLICATION

This is a divisional of U.S. patent application Ser. No. 14/232,603, filed on Jan. 13, 2014, which is the U.S. national stage of PCT Application No. PCT/US2012/047684, filed Jul. 20, 2012, which was published in English under PCT Article 21(2), which claims the benefit of U.S. Provisional Application No. 61/510,387, filed Jul. 21, 2011. The prior applications are incorporated herein by reference in their entirety.

STATEMENT OF GOVERNMENT SUPPORT

This invention was made with United States government support under grant NIHR21AI083389, R01DK088787 and NIH R21HL106325 awarded by the National Institutes of Health; the United States government has certain rights in the invention.

FIELD

This relates to the treatment of hepatitis C virus infection, specifically to the use of apolipoprotein E proteins for the treatment of hepatitis C virus infection.

BACKGROUND

Hepatitis C virus (HCV) is an important human pathogen that primarily infects human hepatocytes and causes many chronic liver diseases. Unfortunately, there is no prophylactic vaccine currently available, and combination therapy with pegylated interferon (IFN)-α and ribavirin is only effective in 40-80% of patients and has severe side effects that results in poor patient compliance. Therefore, new antiviral drugs are urgently needed to treat HCV infection in combination with current therapies.

Research on HCV was revolutionized by the advent of the Japanese fulminant HCV strain (JFH-1) that can be cultivated in cell culture (HCVcc) and hence permits the study of the entire viral life cycle (see, for example, Lindenbach et al., Science 2005; 309:623-626). HCV entry requires at least four cellular membrane proteins, including CD81 (Pileri et al, Science 1998; 282:938-941), scavenger receptor BI (SR-BI)(Scarselli et al., Embo J 2002; 21:5017-5025), claudin-1 (CLDN1)(Evans et al., Nature 2007; 446:801-805), and occludin (OCLN) (Liu, J Virol 2009; 83:2011-2014; Ploss et al., Nature 2009; 457:882-886). Remarkably, another host factor, human apolipoprotein E (apoE), appears to be assembled into infectious virions and plays a crucial role in conferring virus infectivity (see, for example, Chang et al., J Virol 2007; 81:13783-13793). The 299-residue apoE is a main component of lipoproteins in plasma and participates in lipid transport via its ability to bind to multiple cell surface receptors, including low density lipoprotein receptor (LDLR), apolipoprotein E receptor 2 (apoER2), very low density lipoprotein receptor (VLDLR), SR-BI, low density lipoprotein receptor-related protein 1 (LRP1), and heparan sulfate proteoglycan (HSPG) (Bu, Nat Rev Neurosci 2009; 10:333-344), some of which have been implicated in HCV entry (reviewed in Popescu and Dubuisson, Biol Cell 2009; 102:63-74).

Disclosed herein are novel peptide inhibitors of HCV infection derived from human apoE that block HCV binding to cell surface.

SUMMARY

Disclosed herein are several apolipoprotein E (ApoE) polypeptides, and nucleic acids encoding these polypeptides that can be used to inhibit the entry of hepatitis C virus into cells. The polypeptides and nucleic acids can be used to treat or prevent a hepatitis infection in a subject, such as a hepatitis C virus infection.

In some embodiments, the ApoE polypeptides are 27 to 64 amino acids in length and inhibit Hepatitis C Virus (HCV) binding to a cell surface, such as a hepatic cell. The polypeptides include the amino acid sequence set forth as SEQ ID NO: 1. In some embodiments, the polypeptides include an N-terminal cysteine, and can form dimers. Nucleic acids encoding these polypeptides are disclosed, as well as vectors and host cells.

The disclosed polypeptides and polynucleotides can be used to treat a subject, either alone or in conjunction with an additional therapeutic agent.

The foregoing and other features and advantages will become more apparent from the following detailed description of several embodiments, which proceeds with reference to the accompanying figures.

BRIEF DESCRIPTION OF THE FIGURES

FIGS. 1A-1C. A human apoE derived peptide (hEP) suppresses HCV infection. (A) Schematic illustration of apoE protein domains and the amino acid sequences of hEP and mEP peptides. The amino acid sequences shown are hEP-1 (SEQ ID NO: 6) and mEP (SEQ ID NO: 20). (B) Dose dependent inhibition of HCVcc infection by hEP. Huh7.5.1 cells were infected with JFH-1 HCVcc-Luc (MOI~0.5) in the presence of hEP or mEP for 2 hours. After removal of virus and peptides, cells were further incubated for 48 hours prior to luciferase assay. Data are presented as % inhibition relative to control infections in which cells were treated with DMSO (0%). Results are expressed as mean±standard deviation (s.d.) (n=3). (C). Huh7.5.1 cells were treated with hEP or DMSO at indicated doses for 48 hours. The effect of hEP on cell viability was measured by a CellTiter Glo assay kit. Bactobolin, a protein synthesis inhibitor, induced significant cell death at indicated concentrations.

FIGS. 2A-2F. Characterization of the hEP-mediated inhibition of HCVcc infection. (A) hEP inhibited HCVcc infection at multiple MOIs. DMSO was added as the negative control. (B) 20 μg/ml hEP or DMSO was incubated with Huh7.5.1 cells for specified periods of time prior to exposure to HCVcc-luc. Results were calculated as percent infection relative to counts obtained from the DMSO-treated samples (set to 100; n=3). (C & D) Huh7.5.1 cells were infected by HCVpp bearing HCV envelope proteins derived from H77, JFH1, and J6, or VSV-Gpp (MOI~0.5) in the presence of DMSO or hEP at indicated concentrations. In D the hEP was 20 μg/ml and the infectivity of DMSO-treated samples was arbitrarily set to 100%. (E) HIV-1 was produced by transfecting the proviral construct pNL4.3 into 293T cells. Equal amount of virus (MOI~0.5) was added to a HIV reporter cell line TZM-bl that harbors a HIV TAT-dependent luciferase reporter construct in the presence of DMSO or hEP at indicated concentrations. 48 hours post-infection, luciferase activity was measured. (F) DENY (Thailand 16681) was added to a Huh7.5.1 cells in the presence of DMSO, hEP, mEP, IFNα, and Bafilomycin A1 for two hours and then replaced with fresh media. 48 hours post-infection, the infectivity of each virus was determined by calculating the 50% tissue culture infection dose ($TCID_{50}$/ml) following standard protocol based on immunostaining of DENY Prm/E protein (2H2 antibody, ATCC).

FIGS. 3A-3C. Both hEP and mEP mediate plasma cholesterol clearance through hepatic lipoprotein receptors. (A) DMPC binding assay was conducted as described in the examples section. The turbidity of DMPC vesicle solution was monitored by OD490 nm. The curves were representative of two independent experiments. (B) HEK293T cells were loaded with DiI-LDL (5 μg/ml) along with apoE peptide-DMPC particles which competed with DiI-LDL for LDLR binding and LDLR-mediated endocytosis (for 30 min) n=3 for each group. (C) Each peptide (100 μg in 100 μl PBS) was retro-orbitally injected into 6-month-old apoE-/- mice (two mice each group). PBS (100 μl) was injected into two other mice as control. Before (set as 0 min time point) and 5 min, 30 min, 1 h, 2 h, and 4 h after the peptide or PBS injection, 30 μl blood samples were drawn for plasma cholesterol measurement using total Cholesterol Reagent Kit (Raichem, San Diego, Calif.).

Figure 4A:
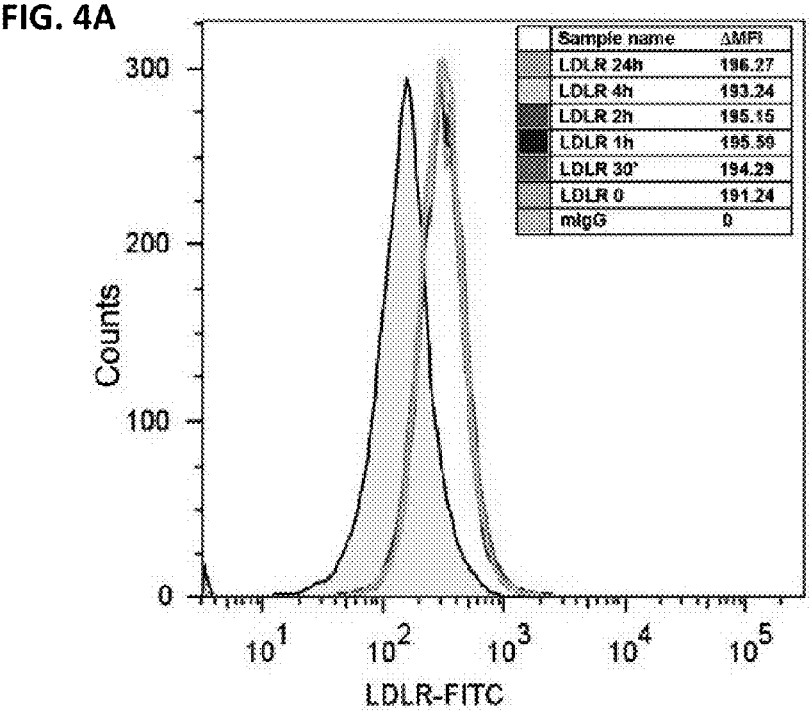
Figure 4B:
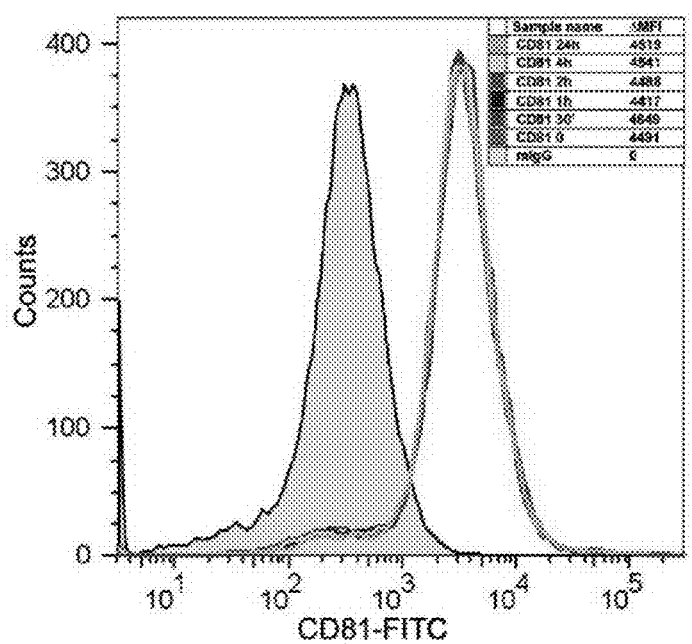
Figures 7A, 7B, 7C:
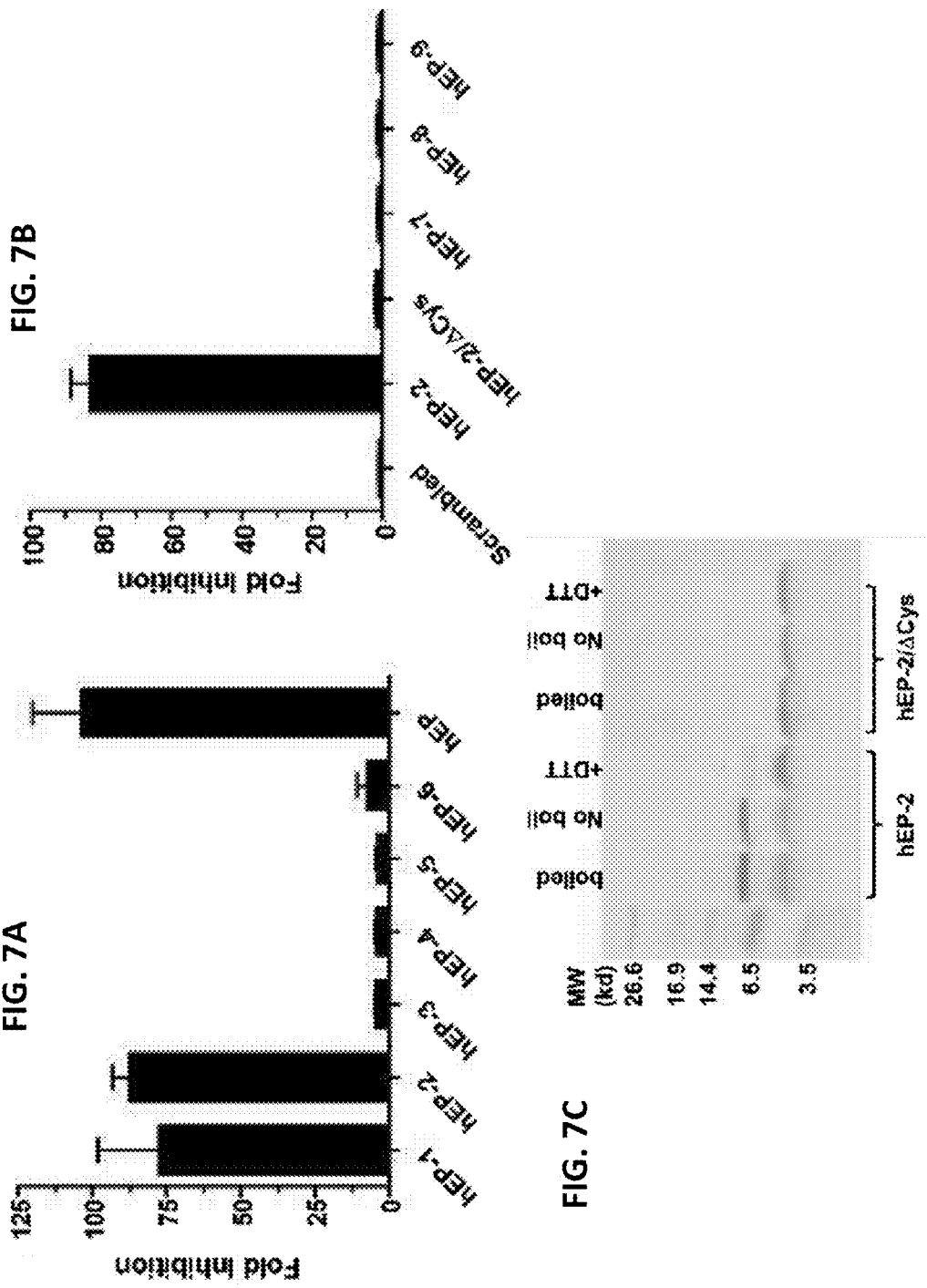
Figure 7E:
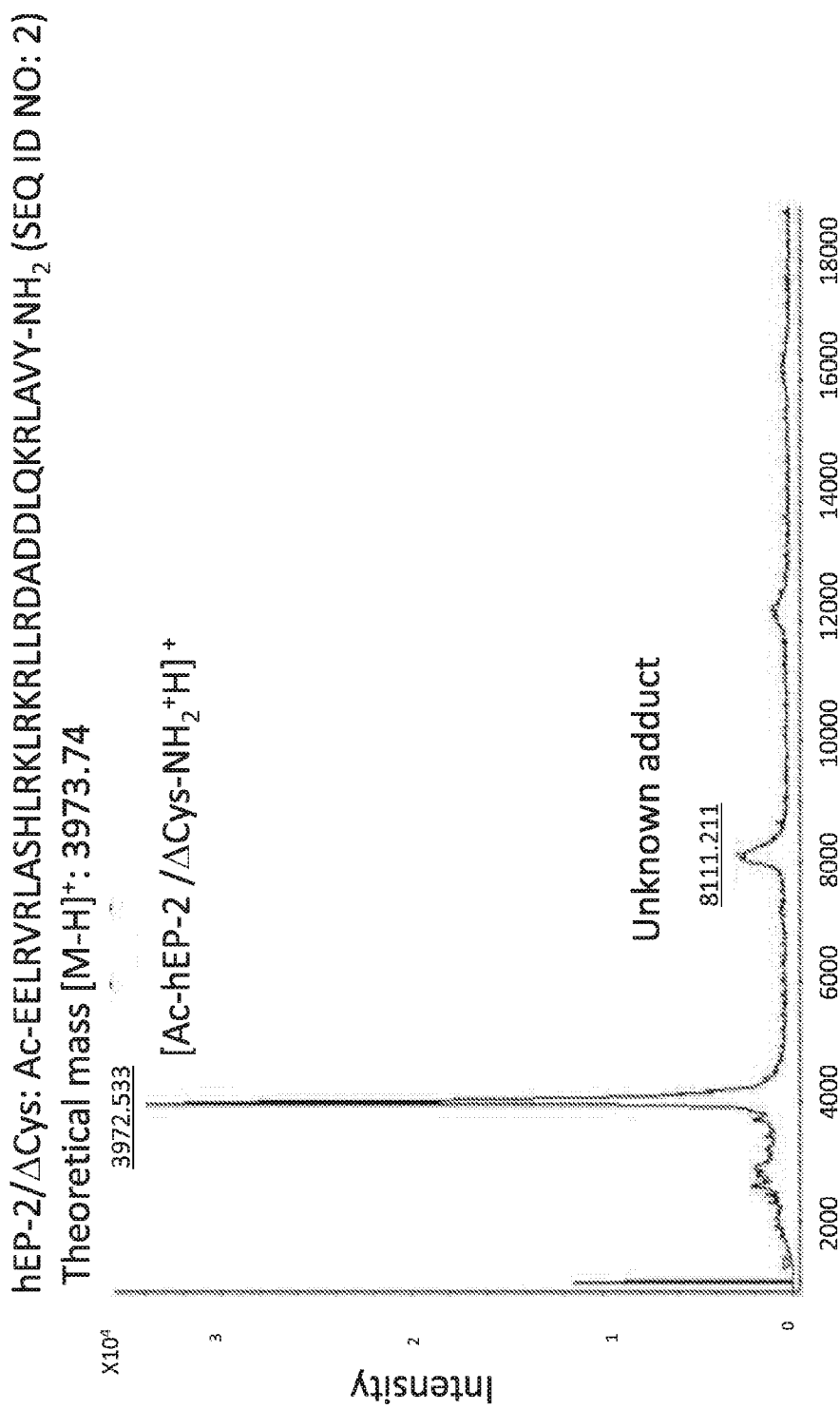

FIGS. 4A-4C. (A) Huh7.5.1 cells seeded in a 12-well plate were treated with hEP-2 (20 μg/ml) for indicated time periods. Cells were stained with a mouse IgG (istotype control) or the anti-LDLR antibody followed by flow cytometric analysis. An overlay of 7 histograms is presented and the Δ median fluorescence intensity (ΔMFI, LDLR stain minus isotype control stain) of each sample is indicated to the upper right of the figure. (B) Cells were stained with anti-CD81 antibody and analyzed similarly as in A. (C) Immunonblots of SR-BI, CLDN1, and OCLN in the presence of hEP-2 or scrambled peptide.

FIGS. 5A-5D. hEP inhibits HCV entry at the attachment step. (A) HCVcc-luc was first mixed with either scrambled peptide or hEP-2 (20 μg/ml) for one hour at room temperature. In Group 1, mixed virus was directly added to Huh7.5.1 cells, whereas in Group 2, virus was purified through ultracentrifuge at 28,000×g for 4 hours in order to remove peptide, and then used to infect Huh7.5.1 cells. $p<0.005$. (B) The kinetics of hEP- and bafilomycin A1-mediated inhibition were determined by time-of-addition assays, as described in the examples section. Fitted lines represent sigmoidal time-dependent curves (mean of n=3; error bars, s.d.). (C) HCVcc-Luc was added to Huh7.5.1 cells at 4° C. and incubated for 1.5 hrs. Unbound virus was removed by 2 washes with cold media, fresh media was added, and the cells were shifted to 37° C. to allow synchronous infection to proceed. Heparin (200 μg/ml), anti-CD81 monoclonal antibody (5 μg/ml), hEP (20 μg/ml), or bafilomycin A1 (10 nM) were present in the media either continuously, during the 4° C. incubation only (attachment), or during the 37° C. incubation phase only (post-attachment). % Inhibition was calculated as 100-percent infection relative to control infections containing DMSO or an isotype antibody control containing 0.01% sodium azide (for anti-CD81 only) (mean of n=3; error bars, s.d.). (D) The effects of hEP (2.7 μM) or scrambled peptide on HCV binding were determined as described in the examples section. Results were calculated as relative RNA copies with numbers obtained from the scrambled peptide treated wells set to 100 (mean of n=3; error bars, s.d.). $p<0.005$.

Figure 6:
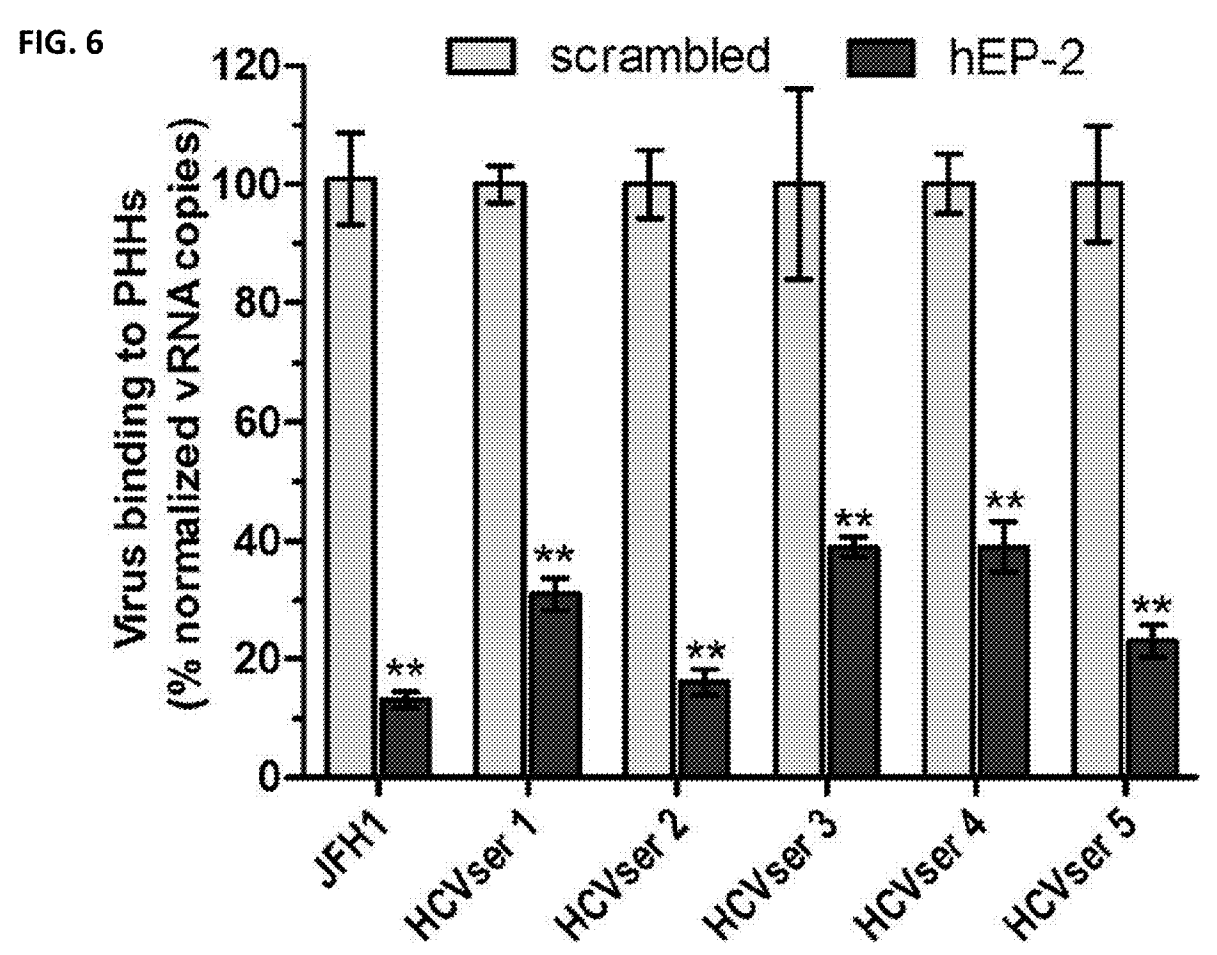

FIG. 6. hEP-2 inhibits binding of HCVser to PHHs. hEP-2 (2.7 μM) or scrambled peptide (2.7 μM) were added together with JFH1 or HCVser 1-5 to PHHs (seeded in a 24-well plate). The binding of virus to cell surface was measured by determining the vRNA copy numbers normalized to the RPS11 RNA level. **$p<0.001$.

FIGS. 7A-7E. Mapping the anti-viral activity of hEP. In (A) and (B), HCVcc-luc was first mixed with indicated peptides (20 μg/ml, 2.7 μM) and then incubated with Huh7.5.1 cells for two hours at 37° C. to initiate infection. After additional 48 hours incubation, luciferase activity was measured. Results are presented as fold of inhibition relative to infections containing DMSO (n=5, mean±sd). (C) 20 μg of hEP-2 or hEP-2/ΔCys were resuspended in PBS and kept at room temperature for 30 minutes. Peptides were then mixed with 2×SDS-sample buffer without DTT and boiled for 5 minutes. Alternatively, samples were simply left unboiled or mixed with sample buffer containing DTT (2 mM). Peptide samples were then subjected to electrophoresis on a 16% tricine non-reducing gel (Invitrogen). The calculated molecular weight of hEP-2 is 4034.82 Da. (D) and (E) Mass spectrometric analysis of hEP-2 or hEP-2/ΔCys. Notice the dimer peak of hEP-2 in (D).

Figure 8:
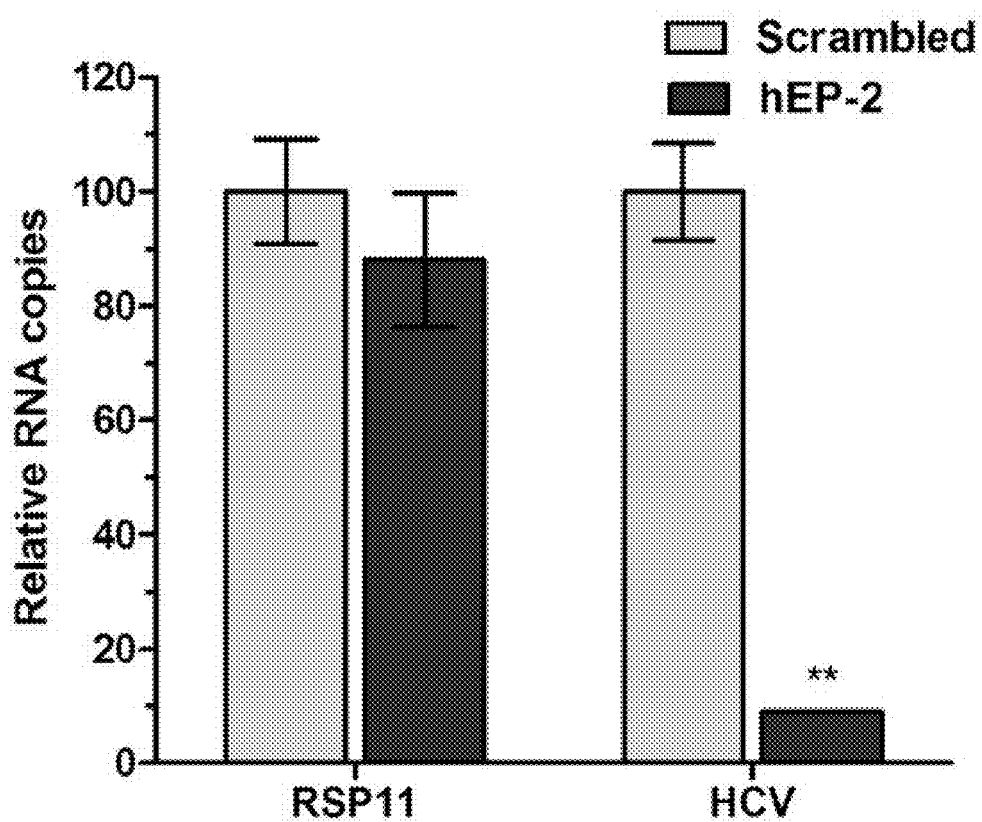

FIG. 8. hEP-2 inhibits HCVcc binding to Huh7.5.1 cells. The effects of hEP-2 (2.7 μM) or scrambled peptide on HCV binding were determined as described in FIG. 5D. Results were calculated as relative RNA copies with numbers obtained from the scrambled peptide treated wells set to 100 (mean of n=3; error bars, s.d.). **$p<0.005$.

SEQUENCE LISTING

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [8123-86640-04_Sequence_Listing.txt, Nov. 24, 2015, 12.5 KB kilobytes], which is incorporated by reference herein.

SEQ ID NO: 1 is the amino acid sequence of hEP-10, lacking the N terminal cysteine.

SEQ ID NO: 2 is the amino acid sequence of hEP-2, lacking the N terminal cysteine.

SEQ ID NO: 3 is the amino acid sequence of human ApoE.

SEQ ID NO: 4 is the amino acid sequence of murine ApoE.

SEQ ID NO: 5 is the amino acid sequence of hEP-3.
SEQ ID NO: 6 is the amino acid sequence of hEP-1.
SEQ ID NO: 7 is the amino acid sequence of a hEP-10 and hEP-3 fusion.
SEQ ID NO: 8 is the amino acid sequence of hEP-10.
SEQ ID NO: 9 is the amino acid sequence of hEP-2.
SEQ ID NO: 10 is the amino acid sequence of hEP-4.
SEQ ID NO: 11 is the amino acid sequence of hEP-5.
SEQ ID NO: 12 is the amino acid sequence of hEP-6.
SEQ ID NO: 13 is the amino acid sequence of hEP-7.
SEQ ID NO: 14 is the amino acid sequence of hEP-8.
SEQ ID NO: 15 is the amino acid sequence of hEP-9.
SEQ ID NO: 16 is the amino acid sequence of hEP-11.
SEQ ID NO: 17 is the amino acid sequence of hEP-12.
SEQ ID NO: 18 is the amino acid sequence of hEP-2/ΔCys.
SEQ ID NO: 19 is the amino acid sequence of scramble hEP-2.
SEQ ID NO: 20 is the sequence of mEP-2.

SEQ ID NOs: 21-24 are the nucleic acid sequences of primers.

DETAILED DESCRIPTION

Hepatitis C virus (HCV) entry is a multiple-step process involving a number of host factors. Isolated human apolipoprotein E (apoE) peptides that block entry of HCV into cells, and thus inhibit HCV infections are disclosed herein. These ApoE polypeptides contain a receptor binding fragment of ApoE and are 27 to 64 amino acids in length. In some embodiments, the proteins include an N-terminal cysteine such that they form dimers.

Isolated nucleic acid molecules encoding any of these polypeptides are also provided. Vectors comprising a promoter operably linked to the isolated nucleic acid molecule are provided. In some embodiments, the vector is a viral vector or a plasmid vector. Host cells transformed with these vectors are disclosed.

Methods are provided for treating a subject with a hepatitis virus infection, such as a hepatitis C virus infection. These methods include selecting a subject with a hepatitis virus infection, and administering a therapeutically effective amount of the polypeptide, or the nucleic acid molecule, thereby treating the subject. In some embodiments, the subject does not have high cholesterol. In additional embodiments, the subject is a human. The method can also include administering a second anti-viral agent to the subject.

In additional embodiments, methods are provided for inhibiting viral replication in a subject infected with a hepatitis virus, such as hepatitis C, comprising administering to the subject a therapeutically effective amount of the polypeptides disclosed herein or a therapeutically effective amount of the nucleic acid molecules disclosed herein, thereby treating the subject. Hepatitis virus is hepatitis C virus. In some examples, the subject is human.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Abnormal: designates a deviation from normal characteristics. Normal characteristics can be found in a control, a standard for a population, etc. For instance, where the abnormal condition is a virus seropositive condition, sources of normal characteristics might include an individual who is not suffering from the disease, a population standard of individuals believed not to be suffering from the disease, etc.

Likewise, abnormal may refer to a condition that is associated with a disease. The term "associated with" includes an increased risk of developing the disease as well as the disease itself. For instance, a certain abnormality (such as an abnormality in liver function) can be described as being associated with the biological conditions of viral infection and tendency to develop decreased liver function.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Animal: a living multicellular vertebrate organism, a category that includes, for example, mammals and birds. A "mammal" includes both human and non-human mammals. Similarly, the term "subject" includes both human and veterinary subjects.

Apolipoprotein E: A class of apolipoprotein found in the chylomicron that binds to a specific receptor on liver cells and peripheral cells. It is essential for the normal catabolism of triglyceride-rich lipoprotein constituents. ApoE is essential for the normal catabolism of triglyceride-rich lipoprotein constituents. In vivo, ApoE transports lipoproteins, fat-soluble vitamins, and cholesterol into the lymph system and then into the blood. It is synthesized principally in the liver, but has also been found in other tissues such as the brain, kidneys, and spleen. In the nervous system, non-neuronal cell types, most notably astroglia and microglia, are the primary producers of ApoE, while neurons preferentially express the receptors for ApoE. The receptor binding fragment of human ApoE includes SEQ ID NO: 1. A human ApoE sequence is provided as GENBANK® Accession No. NP_000032 (Jun. 26, 2011), incorporated by reference herein. The apoE receptor (apoER2) binding domain of apoE is in the 1-165 amino terminal region, whereas the carboxy terminal 230-299 region of apoE is required for efficient initial association with phospholipids. An apoE receptor binding fragment includes at least 25 consecutive amino acids of amino acids 1-165 of apoE, such as at least 27, 28, 29, 30, or 31 consecutive amino acids of this region of apoE. Similarly, an apoE lipid binding fragment includes at least 25 consecutive amino acids of amino acids 230-299 of apoE, such as at least 27, 28, 29, 30, or 31 consecutive amino acids of this region of apoE.

Biological samples: Suitable biological samples include samples containing genomic DNA or RNA (including mRNA), obtained from body cells of a subject, such as those present in peripheral blood, urine, saliva, tissue biopsy, surgical specimen, amniocentesis samples, derivatives and fractions of blood such as serum, and liver biopsy material.

Conservative substitutions: modifications of a polypeptide that involve the substitution of one or more amino acids for amino acids having similar biochemical properties that do not result in change or loss of a biological or biochemical function of the polypeptide. These "conservative substitutions" are likely to have minimal impact on the activity of the resultant protein. In one embodiment, a conservative substitution of a CDR region does not change the antigen binding of the CDR. Table 1 shows non-limiting examples of amino acids that may be substituted for an original amino acid in a protein, and which are regarded as conservative substitutions.

| Original Residue | Conservative Substitutions |
|---|---|
| ala | ser |
| arg | lys |
| asn | gln; his |
| asp | glu |
| cys | ser |
| gln | asn |
| glu | asp |
| gly | pro |

-continued

| Original Residue | Conservative Substitutions |
|---|---|
| his | asn; gln |
| ile | leu; val |
| leu | ile; val |
| lys | arg; gln; glu |
| met | leu; ile |
| phe | met; leu; tyr |
| ser | thr |
| thr | ser |
| trp | tyr |
| tyr | trp; phe |
| val | ile; leu |

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. A cDNA sequence variant may, for example, introduce no more than twenty, and for example fewer than ten amino acid substitutions into the encoded polypeptide. Variant amino acid sequences may, for example, be 80, 90 or even 95% or 98% identical to the native amino acid sequence. Programs and algorithms for determining percentage identity can be found at the NCBI website.

Control: A substance or sample used during a screening or detection assay to aid in gauging the result. For instance, in an assay screening for or detecting HCV, a control might be a sample taken from a subject known to have active HCV infection or a subject known to be free of HCV infection. A control can also be a sample containing a known amount of HCV virions, or a standard curve. A control can be used to gauge the success of the assay itself, and/or to prevent detection of false positives or false negatives in a sample.

DNA: deoxyribonucleic acid. DNA is a long chain polymer that comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Encode: a polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Epitope: the site on an antigen recognized by an antibody as determined by the specificity of the amino acid sequence.

Hepatitis: A disorder in which viruses or other mechanisms (e.g., autoimmune or toxic mechanisms) produce inflammation in liver cells, resulting in their injury or destruction. In most cases this inflammatory process is triggered when the immune system fights off infections caused by viruses. Inflammation of the liver can also occur from medical problems, drugs, alcoholism, chemicals, and environmental toxins. Hepatitis varies in severity from a self-limited condition with total recovery to a life-threatening or life-long disease. Hepatitis manifests as either short-term (acute hepatitis) or prolonged (chronic hepatitis). In some cases, acute hepatitis develops into a chronic condition, but chronic hepatitis can also occur on its own. Although chronic hepatitis is generally the more serious condition, patients having either condition can experience varying degrees of severity. The chronic forms of hepatitis persist for prolonged periods (See Cecil Textbook of Medicine, 19th ed. Wyngaarden, Smith and Bennett eds., W.B. Saunders Co., 1992; WebMD website).

Most cases of hepatitis are caused by viruses that attack the liver. Five hepatitis viruses are known, called hepatitis A virus (HAV), hepatitis B virus (HBV), hepatitis C virus (HCV), hepatitis D virus (HDV), and hepatitis E virus (HEV). HBV is composed of DNA while HAV, HCV, HDV, and HEV are RNA viruses. The viruses for hepatitis are found in semen, blood, and saliva and are usually spread by blood transfusions, contaminated needles, contaminated food and water sources, and exposure to contaminated fecal matter or sexual contact with an infected individual. Hepatitis A virus can be detected in a biological sample using an antibody that exhibits specific binding to the virus capsid.

Hepatitis C Virus (HCV): HCV is a single-stranded positive-sense RNA virus, which is about 9.6 kb in length that causes hepatitis in humans. HCV belongs to the Hepacivirus genus of the family Flaviviridae. The viral RNA genome consists of the 5' untranslated region (5'UTR), a single open reading frame (ORF) encoding a viral polypeptide of 3,010-3,040 amino acids, and the 3' untranslated region (3'UTR) of variable length. Upon translation, the viral polyprotein is cleaved by cellular peptidases and viral proteases into core (C), envelope glycoproteins (E1 and E2), P7, non-structural (NS) proteins NS2, NS3, NS4A, NS4B, NS5A, and NSSB. Sequence analysis and comparison studies have revealed that both the 5'UTR and 3'UTR of the HCV genome are highly conserved. In contrast, sequences of the ORF exhibit a variation among HCV isolates. Based on the nucleotide sequence similarity, HCV has been further grouped into six major genotypes and numerous subtypes.

HCV infection is characterized by the establishment of chronic infection in up to about 85% of individuals exposed to HCV. The chronic HCV infection carries an increased risk of developing fatal liver diseases such as cirrhosis, liver failure, and hepatocellular carcinoma. HCV-associated end-stage liver disease is the leading cause of liver transplantation in the United States (US). It is estimated that approximately 4 million people in the US and 170 million people worldwide are persistently infected with HCV. Each year, HCV infection results in 8,000-10,000 deaths in the US alone.

Immunogen: A compound, composition, or substance which is capable, under appropriate conditions, of stimulating an immune response, such as the production of antibodies or a T-cell response in an animal, including compositions that are injected or absorbed into an animal. As used herein, as "immunogenic composition" is a composition comprising an immunogen (such as a flavivirus E protein).

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Low Density Lipoprotein (LDL): One of the five major groups of lipoproteins, which in order of size, largest to smallest, are chylomicrons, very low density lipoprotein (VLDL), intermediate density lipoprotein (IDL), LDL, and high density lipoprotein (HDL), that enable transport of multiple different fat molecules, including cholesterol, within the bloodstream. Each native LDL particle contains a single apolipoprotein B-100 molecule.

LDL Receptor: A mosaic protein of about 840 amino acids (after removal of signal peptide) that mediates the endocytosis of cholesterol-rich LDL. It is a cell-surface receptor that recognizes the apoprotein B100 which is embedded in the phospholipid outer layer of LDL particles. The receptor also recognizes the apoE protein found in chylomicron remnants and VLDL remnants (IDL).

When a cell requires cholesterol, it synthesizes the necessary LDL receptors, and inserts them into the plasma membrane. The LDL receptors diffuse freely until they associate with clathrin-coated pits. LDL particles in the blood stream bind to these extracellular LDL receptors. The clathrin-coated pits then form vesicles that are endocytosed into the cell.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Peptide modifications: ApoE polypeptides include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the ApoE peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an ApoE polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "fragment" refers to a portion of a polypeptide that is at least 8, 10, 15, 20 or 25 amino acids in length. The term "functional fragments of a polypeptide" refers to all fragments of a polypeptide that retain an activity of the polypeptide (e.g., the binding of an antigen). Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

Preventing, treating or ameliorating a disease: "Preventing" a disease refers to inhibiting the full development of a disease, such as hepatitis. "Treating" refers to a therapeutic intervention that ameliorates a sign or symptom of a disease, such as hepatitis, or related pathological condition after it has begun to develop. "Ameliorating" refers to the reduction in the number or severity of signs or symptoms of a disease, such as hepatitis.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is a CMV promoter.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. The term recombinant includes nucleic acids, proteins and viruses that have been altered solely by addition, substitution, or deletion of a portion of a natural nucleic acid molecule, protein or virus.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals, such as non-human primates.

Therapeutically effective amount or effective amount: A quantity of a specified agent sufficient to achieve a desired effect in a subject being treated with that agent. For example, this may be the amount of an apoE polypeptide sufficient to inhibit viral entry into a cells, or sufficient to block binding of the virus to a cell, or sufficient to for preventing infection by hepatitis virus. With regard to an effective amount, this is an amount sufficient to achieve the desired effect in vitro and/or in vivo.

Ideally, in the context of the present disclosure, a therapeutically effective amount is an amount sufficient to increase resistance to, prevent, ameliorate, and/or treat infection caused by HCV in a subject without causing a substantial cytotoxic effect in the subject. The therapeutically effective amount of a HCV vaccine useful for increasing resistance to, preventing, ameliorating, and/or treating infection in a subject will be dependent on, for example, the subject being treated, the manner of administration of the therapeutic composition and other factors.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides or DNA derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been killed with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes. In some embodiments of the present disclosure, the vector encodes a flavivirus E protein. In some embodiments, the vector is the pTR600 expression vector (U.S. Patent Application Publication No. 2002/0106798; Ross et al., *Nat Immunol.* 1(2):102-103, 2000; Green et al., *Vaccine* 20:242-248, 2001).

Viral Entry: An the early stage of infection in the viral life cycle, as the virus comes into contact with the host cell and introduces viral material into the cell. An agent that inhibits viral entry can the inhibit binding of a virus to receptors on a cell membrane. In some embodiments the agent is a polypeptide, such as, but not limited to, a polypeptide that dimerizes and inhibits viral entry.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Overview of Several Embodiments

Disclosed herein are several apoplipoprotein E (apoE) polypeptides that can be used to treat or prevent an hepatitis C virus (HCV) infection in a subject. These polypeptides include a receptor binding fragment of apoE, and can inhibit entry of hepatitis C virus into cells. In some embodiments, these polypeptides bind low density lipoprotein receptor (LDLR). These polypeptides can inhibit viral entry, and thus can inhibit binding of a virus to receptors on a cell membrane. In some embodiments the polypeptide dimerizes and inhibits viral entry. Thus, the polypeptide can include an N-terminal cysteine that allows the polypeptide to dimerize in vitro and/or in vivo. In other embodiments, the polypeptide inhibits viral entry as a monomer. Generally, the polypeptides do not include full length ApoE. In some embodiments the apoE is human ApoE.

Nucleic acids and vectors encoding these polypeptide are disclosed herein, as are methods of using these polypeptide, nucleic acids and vetors to treat an HCV infection.

ApoE Polypeptides

ApoE polypeptides are disclosed that are 28 to 66 amino acids in length that can inhibit Hepatitis C Virus (HCV) binding to the cell surface. In some embodiments, the ApoE polypeptide is 28-61 amino acids in length. In additional embodiments, the polypeptide is 29-61 amino acids in length. The polypeptide can be 30-61 amino acids in length, 31-61 amino acids in length or 32-61 amino acids in length. In some embodiments the polypeptide is 29-58 amino acids in length. In other embodiments, the polypeptide is 32-58 amino acids in length. In further embodiments, the polypeptide is 29-66 amino acids in length. In other embodiments, the polypeptide is 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63 or 64 amino acids in length. The polypeptide does not include full length ApoE.

In some embodiments, the polypeptides can be longer. Thus, the polypeptides can be 28 to 75 amino acids in length, such as 28 to 100 amino acids in length, 28 to 125 amino acids in length, 28 to 150 amino acids in length, 28 to 200 amino acids in length or 28 to 225 amino acids in length. In other embodiments, the polypeptides can be 29 to 75 amino acids in length, such as 29 to 100 amino acids in length, 29 to 125 amino acids in length, 29 to 150 amino acids in length, 29 to 200 amino acids in length or 29 to 225 amino acids in length. In other embodiments, the polypeptides can be 32 to 75 amino acids in length, such as 32 to 100 amino acids in length, 32 to 125 amino acids in length, 32 to 150 amino acids in length, 32 to 200 amino acids in length or 32 to 225 amino acids in length. In some embodiments, the polypeptide is between 64 and 80 amino acids in length, or is between 64 and 70 amino acids in length. The polypeptide can inhibit the entry of hepatitis C virus into a cell.

These polypeptides include a receptor binding fragment of apoE, and can inhibit entry of hepatitis C virus into cells. In some embodiments, these polypeptides bind low density lipoprotein receptor (LDLR). In some embodiments, the apoE polypeptides mediate plasma cholesterol clearance. An ApoE polypeptide that can inhibit hepatitis C viral entry can the inhibit binding of a hepatitis C virus to receptors on a cell membrane. In some embodiments the polypeptide dimerizes to inhibit viral entry. Thus, a dimer of the polypeptide inhibits entry of hepatitis C virus in vivo and/or in vitro. Similarly, a dimer of the polypeptide binds LDLR in vivo and/or in vitro.

However, in other embodiments, the polypeptide inhibits viral entry as a monomer. Thus, a monomer of the polypeptide inhibits entry of hepatitis C virus in vivo and/or in vitro. Similarly, a monomer of the polypeptide binds LDLR in vivo and/or in vitro.

The apoE polypeptides include the amino acid sequence set forth as:

VRLASHLRKLRKRLLRDADDLQKRLAVY (SEQ ID NO: 1, hEP-10, no C, 28 amino acids in length).

In some embodiments, the polypeptides include the amino acid sequence set forth as:

EELRVRLASHLRKLRKRLLRDADDLQKRLAVY (SEQ ID NO: 2, hEP-2, no N-terminal cysteine, 32 amino acids in length). This polypeptide includes four additional amino acids of the apoE protein N-terminal to SEQ ID NO: 1.

Thus, in some embodiments, the polypeptide can include SEQ ID NO: 1 and additional amino acids of the native ApoE protein. The additional amino acids can be N-terminal and/or C-terminal to the amino acid sequence set forth as SEQ ID NO: 1.

An exemplary human ApoE amino acid sequence is set forth below: MKVLWAALLV TFLAGCQAKV EQAVETEPEP ELRQQTEWQS GQRWELALGR FWDYLRWVQT LSEQVQEELL SSQVTQELRA LMDETMKELK AYKSELEEQL TPVAEETRAR LSKELQAAQA RLGADMEDVR GRLVQYRGEV QAMLGQSTEE LRVRLASHLR KLRKRLLRDA DDLQKRLAVY QAGAREGAER GLSAIRERLG PLVEQGRVRA ATVGSLAGQP LQERAQAWGE RLRARMEEMG SRTRDRLDEV KEQVAEVRAK LEEQAQQIRL QAEAFQARLK SWFEPLVEDM QRQWAGLVEK VQAAVGTSAA PVPSDNH (SEQ ID NO: 3), see also GENBANK® Accession No. AAB59397.1, Nov. 9, 1994, incorporated by reference herein.

An exemplary murine ApoE sequence is set forth below: MKALWAVLLV TLLTGCLAEG EPEVTDQLEW QSNQPWEQAL NRFWDYLRWV QTLSDQVQEE LQSSQVTQEL TALMEDTMTE VKAYKKELEE QLGPVAEETR ARLGKEVQAA QARLGADMED LRNRLGQYRN EVHTMLGQST EEIRARLSTH LRKMRKRLMR DADDLQKRLA VYKAGAREGA ERGVSAIRER LGPLVEQGRQ RTANLGAGAA QPLRDRAQAF GDRIRGRLEE VGNQARDRLE EVREHMEEVR SKMEEQTQQI RLQAEIFQAR LKGWFEPIVE DMHRQWANLM EKIQASVATN PIIT-PVAQEN Q (SEQ ID NO: 4), see also GENBANK® Accession No. AAH28816, Jul. 15, 2006, incorporated by reference herein.

In additional embodiments, the polypeptide can include one or more additional ApoE polypeptide, such as EEQAQQIRLQAEAFQARLKSWFEPLVEDM (SEQ ID NO: 5, hEP-3)

In other embodiments the polypeptide includes, or consists of, the amino acid sequence set forth as:

EELRVRLASHLRKLRKRLLRDADDLQKRLAVY-EEQAQQIRLQAEAF QARLKSWFEPLVEDM (hEP-1, SEQ ID NO: 6, 61 amino acids).

In additional embodiments, the polypeptide includes, or consists of, the amino acid sequence set forth as:

VRLASHLRKLRKRLLRDADDLQKRLAVY-EEQAQQIRLQAEAFQARL KSWFEPLVEDM (SEQ ID NO: 7, 57 amino acids, not synthesized, theoretical HEP-10 and HEP 3 fusion)

However, in some embodiments, the polypeptides can also include additional amino acids that are not included in the native apoE protein.

In some embodiments, the ApoE polypeptide can include a terminal cytosine, for example an N-terminal or a C-terminal cysteine. The ApoE polypeptide can dimerize through this cytosine. In some examples, the ApoE polypeptide includes an N-terminal cytosine.

Thus, in some examples, the polypeptide includes, or consists of the amino acid sequence set forth as:

CVRLASHLRKLRKRLLRDADDLQKRLAVY (SEQ ID NO: 8) (hEP-10)

In additional examples, the polypeptide includes, or consists of the amino acid sequence set forth as:

CEELRVRLASHLRKLRKRLLRDADDLQKRLAVY (SEQ ID NO: 9, hEP-2, 33 amino acids).

Polypeptides that include an N-terminal cysteine form dimers. In some embodiments, the dimer includes two polypeptides, wherein each of the two polypeptides includes the amino acid sequence set forth as SEQ ID NO: 1, and each of the two polypeptides comprises an N-terminal cysteine. In this embodiment, each of the two polypeptides is at most 32 amino acids in length. The polypeptides dimerize by the formation of a cysteine bond between the N-terminal cysteines. In specific, non-limiting examples, the dimer includes (or consists of) two copies of SEQ ID NO: 8 or two copies of SEQ ID NO: 9. These dimers are also of use in the methods disclosed herein.

In additional embodiments, polypeptides are provided that include two copies of SEQ ID NO: 1 or SEQ ID NO: 2 in a linear peptide sequence, connected by peptide bonds. These polypeptides are 56 and 62 amino acids in length, respectively.

In additional embodiments, the ApoE polypeptide includes two copies of SEQ ID NO: 1 or two copies of SEQ ID NO: 2, separated by a linker. Linkers are well known in the art, and include glycine/serine linkers. The polypeptide an also include one copy of SEQ ID NO: 1 in addition to one copy of SEQ ID NO: 2. Optionally, a linker is included between SEQ ID NO: 1 and SEQ ID NO: 2.

Polypeptides 96%, 97%, 98% and 99% identical to amino acid sequence provided in SEQ ID NO: 1, SEQ ID NO: 2, SEQ ID NO: 5, SEQ ID NO: 6, SEQ ID NO: 7 SEQ ID NO: 8 and/or SEQ ID NO: 9 can be included in the ApoE polypeptides disclosed herein. These polypeptides also can inhibit HCV viral entry.

In addition, polypeptides of use can include at most one, at most two, at most three, at most four conservative substitutions in SEQ ID NO: 1, SEQ ID NO: 2, SEQ ID NO: 5, SEQ ID NO: 6, SEQ ID NO: 7 SEQ ID NO: 8 and/or SEQ ID NO: 9. However, if the polypeptide includes an N-terminal cysteine, this amino acid must remain in the polypeptide.

The ApoE polypeptides disclosed herein can be chemically synthesized by standard methods, or can be produced recombinantly. An exemplary process for polypeptide production is described in Lu et al., *Federation of European Biochemical Societies Letters*. 429:31-35, 1998. One method of producing the disclosed polypeptides is to link two or more amino acid residues, peptides or polypeptides together by protein chemistry techniques. For example, peptides or polypeptides are chemically synthesized using currently available laboratory equipment using either Fmoc (9-fluorenylmethyloxycarbonyl) or Boc (tert-butyloxycarbonoyl) chemistry (Applied Biosystems, Inc., Foster City, Calif.). A peptide or polypeptide can be synthesized and not cleaved from its synthesis resin, whereas the other fragment of a peptide or protein can be synthesized and subsequently cleaved from the resin, thereby exposing a terminal group, which is functionally blocked on the other fragment. By peptide condensation reactions, these two fragments can be covalently joined via a peptide bond at their carboxyl and amino termini, respectively, (Grant GA (0.1992) Synthetic Peptides: A User Guide. W.H. Freeman and Co., N.Y. (1992); Bodansky M and Trost B., Ed. (1993). Principles of Peptide Synthesis. Springer-Verlag Inc., NY). Alternatively, the peptide or polypeptide is independently synthesized in vivo. Once isolated, these independent peptides or polypeptides may be linked to form a peptide or fragment thereof via similar peptide condensation reactions. For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)).

The polypeptides can be isolated by methods including preparative chromatography and immunological separations. Furthermore, the ApoE polypeptides can also be produced using standard molecular biology methods, including cloning and expression in host cells.

Nucleic Acids

Isolated nucleic acid molecules are provided herein that include a nucleotide sequence encoding the ApoE polypeptides disclosed herein, wherein the nucleotide sequence does not encode full length ApoE. Also provided are vectors that include the nucleic acid molecules, and isolated host cells comprising the vectors.

Polynucleotides encoding the ApoE polypeptides disclosed herein are also provided. These polynucleotides include DNA, cDNA and RNA sequences which encode the polypeptide of interest, which can include a precursor of a polypeptide of interest, such as a cysteine-containing polypeptide that subsequently diminishes. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding an ApoE polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., Cold Spring Harbor Symp. Quant. Biol. 51:263, 1987; and Erlich, ed., PCR Technology, (Stockton Press, N Y, 1989). Polynucleotides also can be isolated by screening genomic or cDNA libraries with probes selected from the sequences of the desired polynucleotide under stringent hybridization conditions.

The polynucleotides encoding an ApoE polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The ApoE peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the ApoE polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropoulos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a ApoE polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Vectors that encode an ApoE polypeptide generally include at least one expression control element operationally linked to the nucleic acid sequence encoding the ApO polypeptide. The expression control elements are inserted in the viral vector to control and regulate the expression of the nucleic acid sequence. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the ApoE polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the ApoE polypeptide, are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419).

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an ApoE polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Pharmaceutical Composition and Methods of Use

Compositions comprising the disclosed nucleic acid molecules, vectors, ApoE polypeptides, dimers, and host cells are also provided by the present disclosure. In some embodiments, the composition comprises a pharmaceutically acceptable carrier. Also provided is a method of treating or preventing a hepatitis C infection in a subject by administering to the subject an ApoE polypeptide, dimer, nucleic acid encoding the polypeptide, or vector, as described herein, thereby treating or preventing the hepatitis C virus (HCV) infection in the subject. In some embodiments the subject has hepatitis, or is at risk of contracting hepatitis C virus. The subject can be any mammal, including, but not limited to, a human.

Methods are also provided for inhibiting the binding of HCV to the surface of a cell. These methods include contacting a cell with an effective mount of one or more of the ApoE polypeptides or dimers disclosed herein, thereby inhibiting the binding of HCV to the cell surface. In addition, methods are provided for inhibiting HCV entry to a cell. These methods include contacting a cell with an effective amount of one or more of the ApoE polypeptides or dimers disclosed herein, thereby inhibiting entry of the HCV into the cell. The cell can be in vivo or in vitro. In some embodiments, the cell is a hepatocyte.

The compositions disclosed herein can be used prophylactically or for treatment of any subject in a demographic group at significant risk for HCV. Subjects can also be selected using more specific criteria (e.g., drug abusers who use needles, subjects exposed to unsafe blood products, subjects who have had unprotected sex with an infected subject, subjects undergoing tattoos or body piercings). In some embodiments, the subject does not have high cholesterol.

The compositions of the present disclosure are ideally administered as soon as possible after potential or actual exposure to the virus. Alternatively the composition may be administered, for example, following exposure to blood products from an infected individual. Alternatively, once HCV infection has been confirmed by clinical observation or laboratory tests, a therapeutically effective amount of the composition is administered. The subject can have an acute or chronic hepatitis C virus infection. In one embodiment, the dose can be given by frequent bolus administration.

A therapeutically effective amount of a composition for individual patients may be determined by titrating the amount of the composition given to the individual to arrive at the therapeutic or prophylactic effect while minimizing potential side effects. Blood tests can be performed to detect the presence of antibodies to the HCV using an enzyme immunoassay. A recombinant immunoblot assay can be used to verify the immunoassay and viral load can be determined by a HCV RNA polymerase chain reaction Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

The ApoE polypeptides, dimers, nucleic acids encoding these polypeptides, vectors, or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Provided herein are pharmaceutical compositions which include a therapeutically effective amount of the apoE polypeptide, including the dimer (or nucleic acid molecules and/or vectors encoding the apoE polypeptide), alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Particular methods for administering nucleic acid molecules are well known in the art. In some examples, the nucleic acid encoding the apoE polypeptide is administered by injection (such as intramuscular or intradermal injection) or by gene gun.

Administration can be accomplished by single or multiple doses. The dose administered to a subject in the context of the present disclosure should be sufficient to induce a beneficial therapeutic response in a subject over time, or to inhibit or prevent hepatitis virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation. The term "administration" refers to both concurrent and sequential administration of the active agents.

One skilled in the art can readily determine an appropriate effective amount of the ApoE polypeptides, dimers polynucleotides and vectors disclosed herein. Therefore, a therapeutically effective amount of the composition will be sufficient to bring about treatment, such as inhibition or prevention of HCV disease symptoms. The effective amount may be determined by measuring the amount of HCV following administration of the composition. Levels of HCV can be measured by in vitro assays known in the art such as RT-PCR. In some embodiments, the dose of the apoE polypeptide is about 1 to about 100 µg. In particular examples, the dose of the apoE polypeptide is about 5, about 10, about 15, about 20, about 25, or about 50 µg. In other embodiments, the dose of nucleic acid molecule encoding the apoE polypeptide is about 0.02 to about 20 µg. In particular examples, the dose of nucleic acid molecule encoding the apoE polypeptide is about 0.1, about 0.2, about 0.4, about 0.6, about 0.8, about 1.0, about 1.5, about 2.0, about 2.5, about 3.0, about 5.0 or about 10 µg.

The apoE polypeptides, nucleic acid molecules encoding the apoE polypeptides, vectors and compositions described herein can be administered alone or in combination with other therapeutic agents. The present methods also include combinations of the monoclonal antibodies disclosed herein with one or more antiviral drugs useful in the treatment of hepatitis C. For example, the compositions disclosed herein can be administered, whether before or after exposure to the virus, in combination with effective doses of other antivirals, immunomodulators, anti-infectives, or vaccines. For example, the subject can be administered interferon (IFN)-α, such as pegylated IFN-α, and/or ribavirin. In other embodiments, the subject is administered boceprevir (VICTRELIS®) or telaprevir (VX-950) optionally in combination with ribavirin and IFN-α. The apoE polypeptides, nucleic acid molecules encoding the apoE polypeptides, vectors and compositions described herein can be administered with a vaccine, such as TG4040. The vaccine can be an attenuated vaccine or a strain of HCV that induces broad cross-neutralizing antibodies.

The disclosure is illustrated by the following non-limiting Examples.

EXAMPLES

Hepatitis C virus (HCV) entry is a multiple-step process involving a number of host factors and hence represents a promising target for new antiviral drug development. In search of novel inhibitors of HCV infection, a human apolipoprotein E (apoE) peptide, hEP, was produced containing both a receptor binding fragment and a lipid binding fragment of apoE, specifically blocked the entry of cell culture grown HCV (HCVcc) at sub-micromolar concentrations. hEP caused little cytotoxicity in vitro and remained active even if left 24 hours in cell culture. Interestingly, hEP inhibited neither HIV-HCV pseudotypes (HCVpp) nor HIV and Dengue virus (DENY) infection. Further characterization mapped the anti-HCV activity to a 32-residue region that harbors the receptor binding domain of apoE, but this fragment must contain a cysteine residue at the N-terminus to mediate dimer formation. The anti-HCV activity of the peptide appears to be dependent on both its length and sequence and correlates with its ability to bind lipids. Finally, it was demonstrated that the apoE-derived peptides directly blocked the binding of both HCVcc and patient serum-derived virus to hepatoma cells as well as primary human hepatocytes. Thus, these apoE peptides potently inhibit HCV infection and suggest a direct role of apoE in mediating HCV entry.

Example 1

Rational Design of a Human apoE Peptide (hEP) as HCV Entry Inhibitor

Previous studies have revealed that the majority of E2-containing viral particles also contain apoE on their surface (Chang et al., J Virol 2007; 81:13783-13793; Gastaminza et al., J Virol 2010; 84:10999-11009; Merz and Luo, J Biol Chem 2010). In the lipid-free state, apoE contains two independently folded structural domains: the N-terminal four-helix-bundle structure that harbors the LDLR binding region (residues 136-150), and the C-terminal domain containing the major lipid-binding region (residues 245-266) (Hatters et al., Trends Biochem Sci 2006; 31:445-454). A human apoE dual-domain peptide was designed, named hEP, that contains nearly the entire amphipathic helix 4 of the N-terminal domain and the major lipid-binding region of the C-terminal domain (FIG. 1A). It was reasoned that such a peptide will compete with virion-associated apoE for cellular receptors or lipids. For comparison, a similar peptide was designed using sequences derived from the mouse apoE (mEP) (FIG. 1A). Both peptides were expressed in bacteria, affinity purified to >95% purity as determined by HPLC, and were free of endotoxin.

Next, the effects of both peptides on HCVcc infection were assessed. Notably, hEP blocked HCVcc infection with a 50% inhibitory concentration (IC$_{50}$) of 0.67 µM, but mEP did not exert significant inhibitory effect until a much higher concentration of peptide was used (FIG. 1B). hEP also showed no cytotoxicity even at the highest dose we could possibly test (100 µg/ml, ~14 µM; FIG. 1C). Further characterization demonstrated that hEP robustly suppressed HCVcc infection at various MOIs (FIG. 2A). The peptide is also rather stable as its anti-HCV activity was largely retained even after being left in the culture for 24 hours (FIG. 2B). By contrast, hEP did not affect the infectivity of HCVpp, HIV-1, or DENY (FIG. 2C-F). Therefore, hEP appears to act on a target that is specifically required for HCVcc infection.

Example 2 hEP Binds Lipid and Lowers Plasma Cholesterol Level

The design of hEP and mEP enables both lipid binding and receptor binding. To verify this dimyristoylphosphatidylcholine liposome (DMPC vesicles) were assembled in vitro and it was found both hEP and mEP efficiently bound to DMPC, transforming the large vesicles (turbid solution) into smaller particles (clear solution) (FIG. 3A). In addition, peptide-DMPC complexes competed with DiI-labeled LDL in binding to cells (FIG. 3B), suggesting they compete for LDLR. Finally, to test whether the two peptides promote endocytic clearance of plasma lipoproteins, the plasma cholesterol level was measured in mice administered with peptides or PBS. As shown in FIG. 3C, hEP and mEP comparably mediated plasma cholesterol clearance in mice. Taken together, these data indicate that both peptides possess lipid binding and receptor binding activity.

Example 3

Sequence-Activity Analysis of the apoE Peptide

To investigate the requirement of lipid binding and receptor binding for hEP to inhibit HCV entry, the region required for antiviral activity of hEP was fine mapped. To that end, six additional peptides (hEP-1 through hEP-6, Table 1) were first designed and chemically synthesized such that the importance of the LDLR binding, and lipid binding, as well as the peptide length for inhibition of HCV entry could be determined.

hEP-1 (SEQ ID NO: 6) is essentially identical to two regions of hEP and is synthetic. hEP-2 (SEQ ID NO: 9) and hEP-3 (SEQ ID NO: 5) contained the N-terminal and the C-terminal half of hEP, respectively. An extra cysteine residue was added to the N-terminus of hEP-2 and hEP-3 in order to increase peptide stability and potentially facilitate the dimerization so that the peptide length would be approximately the same as hEP-1. hEP-4 (SEQ ID NO: 10) and hEP-5 (SEQ ID NO: 11) are shorter versions of hEP-2 (SEQ ID NO: 9) and hEP-3 (SEQ ID NO: 5) that still contain the consensus LDLR binding region or major lipid binding region, respectively. hEP-6 (SEQ ID NO: 12) is the combination of hEP-4 (SEQ ID NO: 10) and hEP-5 (SEQ ID NO: 11) sequences without the N-terminal cysteine residue. As shown in Table 1 and FIG. 7A, while hEP-1 (SEQ ID NO: 6) and hEP-2 (SEQ ID NO: 9) had similar activity to the original hEP peptide, hEP3 (SEQ ID NO: 5) showed a dramatically reduced ability to inhibit HCVcc entry, possibly due to the loss of the LDLR binding domain. The primary amino acid sequence is critical for antiviral activity because a scrambled peptide based on hEP-2 (scrambled hEP2, SEQ ID NO: 19), and mEP-2 (SEQ ID NO: 20), a peptide derived from mouse apoE gene, both failed to inhibit HCV infection (Table 1).

TABLE 1

The synthetic peptides described in the study

| ID* | Sequence | Corresponding to human apoE sequence | IC$_{50}$ (µM) | DMPC binding | Solubility in water |
|---|---|---|---|---|---|
| hEP-1 | EELRVRLASHLRKLRKRLLRDADDLQKRLAVYEEQAQQIRLQAEAFQARLKSWFEPLVEDM | 131-162 + 244-272 | 0.67 | + | low |
| hEP-2 | CEELRVRLASHLRKLRKRLLRDADDLQKRLAVY | 131-162 | 0.50 | ++ | good |
| hEP-2/ΔCys | EELRVRLASHLRKLRKRLLRDADDLQKRLAVY | 131-162 | >10 | ++ | good |
| Scrambled | CVDRYEARLRARALKDRQKRLLKELSLLVRHLD | 131-162 | >10 | ± | good |
| mEP-2 | CEEIRARLSTHLRKMRKRLMRDADDLQKRLAVY | 131-162 | >10 | ++ | good |
| hEP-3 | CEEQAQQIRLQAEAFQARLKSWFEPLVEDM | 244-272 | >10 | + | low |
| hEP-4 | CVRLASHLRKLRKRLLRDADDL | 135-155 | >10 | − | low |
| hEP-5 | CIRLQAEFQARLKSWFEPLV | 250-269 | >10 | n.d | n.d |
| hEP-6 | VRLASHLRKLRKRLLRDADDLIRLQAEAFQARLKSWFEPLV | 135-155 + 250-269 | >10 | n.d | n.d |
| hEP-7 | LRVRLASHLRKLRKRLLRDADDLQKRLAVY | 133-162 | >10 | n.d | n.d |
| hEP-8 | EELRVRLASHLRKLRKRLLRDADDL | 131-155 | >10 | n.d | n.d |
| hEP-9 | VRLASHLRKLRKRLLRDADDLQKRLAVY | 135-162 | >10 | n.d | n.d |
| hEP-10 | CVRLASHLRKLRKRLLRDADDLQKRLAVY | 135-162 | 0.80 | ++ | good |
| hEP-11 | CLRVRLASHLRKLRKRLLRDADDL | 133-155 | 4 | − | low |
| hEP-12 | CLRKLRKRLLRC | 141-150 | >10 | − | low |

The DMPC binding assay requires all peptides to be dissolved in aqueous solution. The solubility of each peptide under such condition is determined by formation of visible precipitates at 0.22 mg/ml. "Good" represents no visible precipitate, whereas "low" indicates partially dissolved. For DMPC binding assays, the binding was quantified as the reduction (percentage) of the turbidity (OD490nm) of DMPC solution, which normally plateaus 10 minutes after the addition of a peptide. −, reduction < 10%; +/−, reduction 10-25%; +, reduction 25-50%; ++, reduction > 50%; n.d, not determined.
*hEP-1 is SEQ ID NO: 6; hEP-2 is SEQ ID NO: 9; hEP-3 is SEQ ID NO: 5; hEP-4 is SEQ ID NO: 10; hEP-5 is SEQ ID NO: 11; hEP-6 is SEQ ID NO: 12; hEP-7 is SEQ ID NO: 13; hEP-8 is SEQ ID NO: 14; hEP-9 is SEQ ID NO: 15; hEP-10 is SEQ ID NO: 5; hEP-11 is SEQ ID NO: 16; hEP-12 is SEQ ID NO: 17; hEP-2/ΔCys is SEQ ID NO: 18; scrambled hEP-2 is SEQ ID NO: 19; mEP-2 is SEQ ID NO: 20.

The length of the peptide was important, because both hEP-6 (SEQ ID NO: 12) and hEP-4 (SEQ ID NO: 10) lost all the inhibitory activities compared to their longer counterparts, hEP-1 (SEQ ID NO: 6) and hEP-2 (SEQ ID NO: 9), respectively. To further test this hypothesis, a hEP-2 peptide lacking the N-terminal cysteine (Designated hEP-2/ΔCys, SEQ ID NO: 2) was syntheshized. It was observed that hEP-2/ΔCys (SEQ ID NO: 2) only existed as monomer and failed to inhibit HCV infection (FIG. 7). Additionally truncated peptides without N-terminal cysteine (hEP-7-9, SEQ ID NOs: 13-15, Table 1), even though they contain the essential LDLR binding region (Dobson et al., J Infect Dis 2006; 193:442-450, 2006), all failed to inhibit HCV. Moreover, three peptides that are shorter than hEP-2 (SEQ ID NO: 9), even though they contain the N-terminal cysteine (hEP-11-12, SEQ ID NOs: 16-17, Table 1), displayed reduced or no inhibitory effect, suggesting the hEP-2 contains the length essential to maintaining the maximal anti-HCV activity.

The above results indicate the C-terminal lipid binding region of apoE is not required for peptides to inhibit HCV infection. However, in the subsequent DMPC binding assay most peptides, except hEP-4, 11, and 12 (SEQ ID NOs: 10, 16 and 17), were able to bind DMPC efficiently (Table 1). Interestingly, hEP-4, 11, and 12 (SEQ ID NOs: 10, 16 and 17) had marginal or no inhibition on HCV entry in comparison to hEP-2 (SEQ ID NO: 9). Altogether, these results suggest that shorter peptides, such as hEP-2 (SEQ ID NO: 9), still bind lipids. Moreover, the lipid-binding ability of a peptide appears to be necessary but not sufficient for inhibiting HCV.

Example 4 hEP does not Decrease the Level of LDLR on Cell Surface

Because the administration of hEP resulted in clearance of plasma cholesterol in mice, it is possible that hEP reduces the surface level of LDLR and hence inhibits HCV infection. To test the hypothesis, Huh7.5.1 cells were treated with hEP for various time periods and quantified the level of LDLR on cell surface by flow cytometry. hEP did not cause detectable change of surface LDLR (FIG. 4), although it cannot be completely ruled out that hEP might have an effect on another receptor that is known to bind apoE. Similarly, hEP did not affect the levels of CD81, SR-BI, CLDN1, and OCLN.

Example 5 hEP Blocks HCV Binding

To investigate the mechanistic action of hEP, three sets of experiments were conducted. First, hEP-2 (SEQ ID NO: 9) or scrambled peptide-treated HCVcc were purified through ultracentrifugation to remove the peptide and then used to infect naïve Huh7.5.1 cells. Both samples displayed equal infectivity, indicating hEP does not directly inactivate virus (FIG. 5A). Second, to determine the kinetics of inhibition, a time-of-addition experiment was conducted. HCV remained sensitive to bafilomycin A1, a fusion inhibitor that prevents endosome acidification, until 3 hours after the 37° C. temperature shift (FIG. 5B), which is consistent with previous reports (Koutsoudakis et al., J Virol 2006; 80:5308-5320). By contrast, hEP activity disappeared almost completely when added after the temperature shift, indicating it acts upon a very early step in virus entry. In order to determine whether hEP-2 (SEQ ID NO: 9) blocks infection at the initial attachment step or a downstream event in the HCV entry process, hEP-2 (SEQ ID NO: 9) was either added together with HCVcc to cells during the 4° C. attachment step only, and then removed prior to shifting the temperature to 37° C., or added only after the temperature shift. As a positive control, hEP-1 was present during the entire course of the experiment. Independent control inhibitors included heparin, the CD81 blocking antibody, and bafilomycin A1. Shown in FIG. 5C, all of the inhibitors and peptides suppressed HCV infection if present throughout the course of the experiment Inhibition by heparin was predominant when added during the 4° C. attachment step, while bafilomycin A1 was most effective during the post-attachment stage. The anti-CD81 antibody was effective when added prior to the temperature shift and remained active even after the temperature shift, which is consistent with what has been reported (Evans et al., Nature 2007; 446:801-805). Hep-1 exhibited very little inhibition when added after the temperature shift, but strongly inhibited viral infection when added during the 4° C. attachment step. Taken together, these data demonstrate that hEP blocks HCV entry at the attachment stage. Finally, the direct binding of virions to cell surface was measured using a real-time PCR based assay. Shown in FIG. 5D, the amount of viral RNA (vRNA) decreased significantly in samples isolated from Hep-1-treated cells, indicating a reduction of binding of HCV to cells. The same observation was made when hEP-2 was added (FIG. 8).

Example 6 hEP Blocks Patient Serum-Derived HCV Binding to Primary Human Hepatocytes (PHHs)

Evidence has suggested structural difference between virions produced in vitro and in vivo in their association with host lipoproteins (Merz et al., J Biol Chem 2010; Bartenschlager and Pietschmann, Proc Natl Acad Sci USA 2005; 102:9739-9740). Primary human hepatocytes (PHHs) then differ from hepatoma cells in many ways which could influence virus entry. To verify the above observations, serum-derived HCV (HCVser) from five patients were incubated with PHHs in the presence of hEP-2 (SEQ ID NO: 9) or the scrambled peptide (SEQ ID NO: 19). Shown in FIG. 6, hEP-2 (SEQ ID NO: 9) markedly reduced the binding of all five HCVser to PHHs albeit to slightly different degrees. The binding of JFH1 to PHHs was also significantly inhibited by hEP-2 (SEQ ID NO: 9).

The host cell-derived protein apoE is a component of the infectious viral particles and contributes to virus infectivity. HCV circulating in blood is in complex with lipoproteins, including apoE (Popescu et al., Biol Cell 2009; 102:63-74; Andre et al., J Virol 2002; 76:6919-6928; Andre et al., Semin Liver Dis 2005; 25:93-104; Nielsen et al., J Virol 2006; 80:2418-2428). There are dual roles of apoE in viral infectivity and assembly (Chang et al., J Virol 2007; 81:13783-13793; Jiang et al., J Virol 2009; 83:12680-12691). The formation of infectious HCV particles requires interaction of NS5A with apoE through a C-terminal α-helix domain of apoE (Cun et al., J Virol 2010; 84:11532-11541; Benga et al., epatology 2010; 51:43-53). It has been proposed that lipoviral particles (LVPs) can attach to cells via low-affinity interactions with HSPG or LDLR, which are likely facilitated by apoE packaged into virions (Owen et al., Virology 2009; 394:99-108; Hishiki et al., J Virol 2010; 84:12048-12057). The results presented herein demonstrate that the hEP peptide blocks the binding of virus to cells, suggesting a role of apoE at the very early stage of HCV entry. The data support a model that hEP competes with viral particles for surface receptors during the attachment stage. Of note, the anti-HCV activity of apoE-derived peptides was retained in a 33-mer synthetic peptide that forms dimer. However, this activity was not found in shorter peptides harboring the minimal receptor binding region of apoE. Those shorter peptides, while previously shown to display antimicrobial activity (Dobson et al., J Infect Dis 2006; 193:442-450; Azuma et al., Peptides 2000; 21:327-330), all failed to block HCVcc infection (Table 1). Without being bound by theory, it is likely due to the influence of peptide length on its structure in solution.

A number of apoE peptides have previously been reported to lower blood cholesterol (Nikoulin et al., J Clin Invest 1998; 101:223-234) and alleviate inflammation (Datta et al., Atherosclerosis 2010; 208:134-141; Lynch et al., J Biol Chem 2003; 278:48529-48533). The hEP used in this study could also mediate plasma cholesterol clearance. Interestingly, both altered lipid profile and chronic inflammation are major problems associated with chronic HCV infection (Levrero, Oncogene 2006; 25:3834-3847; Negro, ut 2010; 59:1279-1287). Thus, a pleotropic apoE peptide is an ideal antiviral candidate.

hEP's anti-viral activity was limited to HCVcc. While HCVpp is thought to enter cells in a manner analogous to authentic HCV, subtle differences between the two experimental systems have been reported (Keck et al., J Virol 2007; 81:1043-1047). The finding that hEP inhibited HCVcc but not HCVpp underscores the difference between the two systems.

HCVpp (HCV pseudoparticles, HCVpp are formed by incorporation of the full-length hepatitis C virus glycoproteins E1 and E2 onto lenti- or retroviral core particles) is typically produced in 293T cells, which do not produce endogenous apoE. In support, the anti-apoE antibody blocked HCVcc (a recently described HCV genotype 2a infectious clone that replicates and produces infectious virus in cell culture) but not HCVpp infection of hepatoma cells (Albecka et al., Hepatology 2011). Without being bound by theory, the presence of apoE may potentially contribute to HCVcc entry in two ways. First, apoE binding to the LDLR is known to trigger endocytosis (Bu, Nat Rev Neurosci 2009; 10:333-344); therefore an intriguing question is whether apoE-containing viral particles become internalized via an apoE-mediated pathway. A recent report suggests, however, this pathway leads to degradation of internalized virions. Alternatively, apoE may merely facilitate the initial attachment of the virus to the cell surface prior to the association between viral envelope proteins and SR-BI/CD81. In this case, apoE would function more like an adhesion molecule, similar to those found in many other virus entry processes that stabilize virus-cell contact to initiate entry (Jolly et al., Traffic 2004; 5:643-650). Two peptides derived from mouse apoE sequence (mEP and mEP-2) failed to inhibit HCV entry.

The identification of apoE peptides now adds to the armamentarium of antiviral drugs that target HCV entry. These reagents will also aid in dissecting the molecular mechanisms of HCV entry. While most of small molecule inhibitors that have advanced to the clinic target viral components, the apoE peptides described here offer advantages as they target a cellular protein that are important for HCV infection and reduce the likelihood of developing resistance. By virtue of its distinct mechanism of inhibition, hEP may be used in combination with other anti-HCV drugs for potential synergistic effects in treating HCV infections.

Example 7

Materials and Methods

Cells and Reagents.

The human kidney epithelial cell line Lenti-X 293T was purchased from Clontech. The Huh7.5.1 line generated from a cured HCV replicon cell line was provided (Zong et al., Proc Natl Acad Sci USA 2005; 102:9294-9299). Maintenance of cell lines has been previously described (Liu et al., Virology 2010; 407:160-170). Normal human hepatocytes were either obtained through the Liver Tissue Cell Distribution System or purchased from Celsis, Inc (Maryland, Md.) and maintained as previously described (Liu et al., Virology 2010; 407:160-170). Antibodies were purchased from BD Biosciences (anti-CD81, JS-81 clone; anti-LDL-R, #550495). Secondary antibodies were purchased from Jackson ImmunoResearch Laboratories, Inc, and Molecular Probes (Invitrogen). Heparin and Bafilomycin A1 were purchased from Sigma.

Statistical Analysis.

Bar graphs were plotted to show mean±standard deviation (SD) of at least two independent experiments. Statistical analyses were performed using Graphpad Prism 5. A p value of <0.05 in the Student's test was considered statistically significant.

Animals.

ApoE deficient (apoE−/−) mice were purchased from the Jackson Laboratory (Bar Harbor, Me.).

Peptides.

To generate the original hEP and mEP peptides, oligonucleotides and primers were custom synthesized by Invitrogen. Gene synthesis PCR was performed using PCR kit from New England Biolab (NEB). Bacterial expression vector pTWIN1 was purchased from NEB. Competent cell BL21pLyss was purchased from Novagen. Chitin beads were purchased from NEB, and Heparin Sepharose CL-6B resin from GE Healthcare. Peptides were expressed through *Escherichia coli* BL21pLysS cells. Bacterial cultures were grown at 37° C. until they reached OD at 600 nm of 1.0. Expression was then induced by 0.5 mM Isopropyl β-D-1-thiogalactopyranoside (IPTG) and continued at 25° C. for 8 hrs. The cells were harvested by centrifugation. The cell pellet was resuspended with Buffer B1 (20 mM Tris-HCl, pH8.5, 500 mM NaCl and 1 mM EDTA) and lysed by sonication. A two-step procedure was then used to purify the peptides. First, the cell extract was loaded onto a chitin bead column and washed with Buffer B1 to remove unbounded proteins. The on-column cleavage of the intein-tag was induced by equilibrating the chitin beads in Buffer B2 (20 mM Tris-HCl, pH 7.0, 500 mM NaCl and 1 mM EDTA) overnight at room temperature, and the target peptide was then eluted with more volume of Buffer B2. Second, the eluted peptide was diluted 1:10 with 10 mM phosphate binding buffer (pH 7.4) containing 100 mM NaCl and loaded to a Heparin Sepharose CL-6B column (GE Healthcare). It was then washed with 15 column volumes of the same binding buffer containing 200 mM NaCl to remove trace unbound intein and CBD, as well as other contaminating proteins. The target peptide was eluted by the binding buffer with increasing concentrations of NaCl. The fractions containing 500-600 mM NaCl were pooled and dialyzed against 10 mM $NH_4HCO_3$, and lyophilized to yield peptide powder.

Subsequent apoE peptides (hEP1-12, Table 1) were chemically synthesized by Lifetein LLC and were >95% pure as determined by HPLC. Lyophilized peptides were reconstituted with DMSO to a concentration of 20 mg/ml as a stock solution and stored at −20° C. In all experiments, the amount of DMSO was kept under 0.5% (v/v) except when higher concentrations of peptides were needed (DMSO was 1% in those cases).

Production and Infection of HCVpp and HCVcc.

Detailed procedures involving the production and use of HCVpp and HCVcc have been published elsewhere (Liu et al., J Virol 2009; 83:2011-2014; Yang et al., Hepatology 2008; 48:1396-1403; Yang et al., J Biol Chem 2008; 283: 8643-8653). Production procedure of HCVcc expressing firefly luciferase that was inserted between NS5A and NS5B (JFH-1 strain) was described elsewhere (Liu et al., Virology 2010; 407:160-170). Unless otherwise indicated, viruses were typically added to cells for two hours before removal. Cells were incubated for additional 48 hours followed by luciferase assay. When purification was needed, HCVcc were subjected to ultracentrifugation (SW41, 28,000×g) for 4 hours through a 20% sucrose cushion. Deidentified human sera, collected from five patients containing high-titer HCV (HCVser), were obtained. The genotype and vRNA copy number of each HCVser has been previously determined by the serum bank and summarized in the Table below:

| LSB ID* | Banking date | viral counts | genotype |
|---------|--------------|--------------|----------|
| 6227 | 24 Oct. 2011 | 8,330,000 | 1a |
| 6228 | 24 Oct. 2011 | 4,790,000 | 1 |
| 6231 | 11 Oct. 2011 | 1,660,000 | 1a |
| 6232 | 26 Oct. 2011 | 1,170,000 | n.d. |
| 6240 | 9 Nov. 2011 | 2,396,361 | 1a |

LSB ID is assigned to each patient. Viral count is defined as the viral genome copy number/milliliter.
n.d. not determined Cytotoxicity/Cell Viability Assay.

Huh7.5.1 cells ($10^5$ per well) were treated with hEP or DMSO at various concentrations for 48 hours in 24-well plates. The numbers of viable cells in culture were determined using the CELLTITER-GLO® Cell Viability Luminescent Assay kit according to the manufacturer's instruction (Promega).

DMPC Binding Assay.

1,2-dimyristoyl-sn-glycero-3-phosphatidylcholine (DMPC) (Avanti Polar Lipids Inc., Alabaster, Ala.) was dissolved in chloroform: methanol (3:1, v/v). It was dried thoroughly under a stream of N2. The dried lipid sample was dispersed in pre-warmed buffer (10 mM Tris-HCl, pH7.2; 150 mM NaCl; 0.5 mM EDTA) to final lipid concentration of 10 mg/ml, vortexed for 1 min, and sonicated 10 times at lowest power for 10 seconds at 24° C. The peptide solution, lipid solution and buffer were all maintained at 23.9° C. One milliliter buffer and 250 μg (25 μl lipid solution) were added in a quartz cuvette, and let equilibrate for 10 min, resulting in a turbid DMPC vesicle solution. Peptide solution (250 μg in 100 μl) was then added to turbid solution in the cuvette, the solution was mixed immediately, and the change of turbidity was monitored by OD at 490 nm as a function of time. If the peptide binds to DMPC vesicles, the large DMPC vesicles will be transformed into smaller DMPC-peptide particles, reducing the turbidity of the solution.

Competitive LDLR Binding Assay.

DiI-LDL (3,3'-dioctadecylindocarbocyanine-low density lipoprotein) was bought from Invitrogen. The lipophilic dye DiI only becomes highly fluorescent and photostable when incorporated into cell membranes. Therefore DiI-LDL has been widely used in studies of LDLR-mediated metabolism of LDL. Receptor-specific binding of DiI-LDL is reflected as an increase in the fluorescence intensity per cell and hence serves as an indication of LDLR presence (McNutt et al., J Biol Chem 2009; 284:10561-10570). HEK293T cells were cultured in 6-well plates at a density of $0.5 \times 10^6$ cells/well overnight. The next day, cells were incubated with DiI-LDL (5 μg protein/ml) for 30 min at 37° C. along with apoE peptide-DMPC at indicated peptide concentrations. After binding, cells were washed three times in ice-cold PBS and percentages of DiI-LDL positive cells were measured by flow cytometry.

Mass Spectrometric Analysis of the Peptides.

After the (hEP-2 and hEP-2/ΔCys) peptides were incubated in water for 30 minutes, the peptide solutions were mixed with the PROTEINCHIP® SPA matrix solution (Bio-rad) at 1:1 ratio (V/V). Subsequently, 1 μL of the mixture was deposited onto a stainless steel MALDI sample target and air-dried to allow for crystal formation. Afterward peptide mass was measured using an Ultraflex MALDI-TOF/TOF mass spectrometer (Bruker, Bremen, Germany) equipped with a 337-nm nitrogen laser. Prior to peptide analysis, the MALDI-TOF/TOF mass spectrometer was calibrated in a mass range of 4,000-20,000 Da using a manufacturer provided protein calibration standard containing insulin, ubiqitin I, cytochrome c, and myoglobin.

Time-of-Addition Assays:

HCVcc-Luc was added to Huh7.5.1 cells at 4° C. and incubated for 2 hrs. Unbound virus was washed off with cold media, and the cells were shifted to 37° C. (set as 0 hr time point) to initiate synchronous infection. At the indicated time points, 20 μg/ml (2.7 μM) hEP (open circles and solid line) or 10 nM bafilomycin A1 (solid circles and dashed line) was added into the media and incubated for two hours prior to removal (exception is t=−2 hr where inhibitors were added back after removal of the virus and incubated for additional two hours prior to removal). Infected cells were incubated at 37° C. for an additional 48 hours prior to luciferase assay Inhibition was calculated as % relative to infections containing inhibitors when added at 5 hrs post temperature shift (100%), and those containing DMSO (0%). Fitted lines represent sigmoidal time-dependent curves (mean of n=3; error bars, s.d.).

HCVcc Binding Assay.

JFH1 HCVcc was added to Huh7.5.1 cells, seeded as triplicates in 12-well plates ($8 \times 10^4$ cells/well), in the presence or absence of specified inhibitors for 2 hours at 4° C. with gentle rocking (MOI~1). Cells were then washed three times with cold phosphate buffered saline (DPBS), followed by total RNA isolation with TRIZOL® reagent (Invitrogen). Quantification of RNA was conducted using QUANTI-FAST® RT-PCR Kit (Qiagen) with an in-house developed protocol on a Step One Real-Time PCR system (Applied Biosystems). Primer sequences for the HCV RNA genome were forward: 5'-GCCTAGCCATGGCGTTAGTA-3' (SEQ ID NO: 21) and reverse: 5'-CTCCCGGGGCACTCG-CAAGC-3' (SEQ ID NO: 22) and for the housekeeping gene RSP11 RNA forward: 5'-GCCGAGACTATCTGCACTAC-3' (SEQ ID NO: 23) and reverse: 5'-ATGTCCAGCCTCA-GAACTTC-3' (SEQ ID NO: 24). The copy number of HCV RNA was calculated by comparing to a standard curve obtained with serial dilutions of a full-length HCV genome encoding plasmid.

It will be apparent that the precise details of the methods or compositions described may be varied or modified without departing from the spirit of the described invention. We claim all such modifications and variations that fall within the scope and spirit of the claims below.

The invention claimed is:

1. A non-naturally occurring isolated polypeptide consisting of the amino acid sequence of SEQ ID NO: 8 or the amino acid sequence of SEQ ID NO: 9.

2. The non-naturally occurring isolated polypeptide of claim 1, consisting of the amino acid sequence of SEQ ID NO: 8.

3. The non-naturally occurring isolated polypeptide of claim 1, consisting of the amino acid sequence of SEQ ID NO: 9.

4. A dimer comprising two identical polypeptides, each with an N-terminus and a C-terminus, wherein each of the two polypeptides consists of the amino acid sequence of SEQ ID NO: 8 or the amino acid sequence of SEQ ID NO: 9, wherein the dimer inhibits the entry of hepatitis C virus into a host cell.

5. A composition comprising an effective amount of an isolated polypeptide consisting of the amino acid sequence of SEQ ID NO: 8 or the amino acid sequence of SEQ ID NO:9 or a dimer comprising two identical polypeptides, wherein each of the two polypeptides consists of the amino acid sequence of SEQ ID NO:8 or the amino acid sequence of SEQ ID NO:9, and a pharmaceutically acceptable carrier.

6. The dimer of claim 4, wherein each of the polypeptides consists of the amino acid sequence of SEQ ID NO: 8.

7. The dimer of claim 4, wherein each of the polypeptides consists of the amino acid sequence of SEQ ID NO: 9.

8. A pharmaceutical composition comprising an effective amount of the dimer of claim 4, and a pharmaceutically acceptable carrier.

9. A pharmaceutical composition comprising an effective amount of the dimer of claim 7, and a pharmaceutically acceptable carrier.

10. A pharmaceutical composition comprising an effective amount of the dimer of claim 6, and a pharmaceutically acceptable carrier.

11. A method of inhibiting the entry of hepatitis C virus into a host cell, comprising, contacting the host cell with an effective amount of the polypeptide or dimer of claim 5, thereby inhibiting entry of the hepatitis C virus into the cell.

12. The method of claim 11, wherein the host cell is in vitro.

13. The method of claim 11, wherein the host cell is in vivo.

14. The method of claim 11, wherein the polypeptide consists of the amino acid sequence of SEQ ID NO: 8.

15. The method of claim 11, wherein the polypeptide consists of the amino acid sequence of SEQ ID NO: 9.

* * * * *